United States Patent [19]
Ratner et al.

[11] Patent Number: 6,131,580
[45] Date of Patent: Oct. 17, 2000

[54] TEMPLATE IMPRINTED MATERIALS BY RFGD PLASMA DEPOSITION

[75] Inventors: Buddy D. Ratner; Huaiqiu Shi, both of Seattle, Wash.

[73] Assignee: The University of Washington, Seattle, Wash.

[21] Appl. No.: 09/293,460

[22] Filed: Apr. 15, 1999

Related U.S. Application Data

[60] Provisional application No. 60/082,150, Apr. 17, 1998.

[51] Int. Cl.⁷ ..................................................... A61B 19/00
[52] U.S. Cl. .................. 128/898; 623/11.11; 623/23.75; 623/23.76; 427/2.24; 427/447
[58] Field of Search ..................................... 128/898, 897; 623/11, 66, 11.11, 23.75, 23.76; 427/2.1, 2.24, 446, 447; 424/422

[56] References Cited

U.S. PATENT DOCUMENTS

| | | |
|---|---|---|
| 4,656,083 | 4/1987 | Hoffman et al. . |
| 4,909,908 | 3/1990 | Ross et al. ............................... 204/1 T |
| 5,034,265 | 7/1991 | Hoffman et al. . |
| 5,153,072 | 10/1992 | Ratner et al. . |
| 5,429,735 | 7/1995 | Johnson et al. .......................... 204/403 |

OTHER PUBLICATIONS

Flam, F., "Molecular Imprints Make a Mark", *Science*, vol. 263, pp. 1221–1222, Mar. 4, 1994.
Srauss, E., "New Ways to Probe the Molecules of Life," *Science*, vol. 282, pp. 1407–1407, Nov. 20, 1998.

*Primary Examiner*—Dinh X. Nguyen
*Attorney, Agent, or Firm*—Christensen O'Connor Johnson & Kindness PLLC

[57] ABSTRACT

Template-imprinted structures 10 are provided having at least one template-imprinted surface 12 defining indentations 14 that are capable of specifically binding cells and/or molecules, such as macromolecules including proteins, peptides and nucleic acids. Presently preferred embodiments of the template-imprinted structures include medical prostheses, such as artificial joints and heart valves, having surface indentations that specifically bind proteins and/or cells that enhance the biocompatibility of the prosthesis, thereby making it less likely that the prosthesis will be rejected by the body. Methods are also provided for making the template-imprinted structures of the present invention.

12 Claims, 30 Drawing Sheets

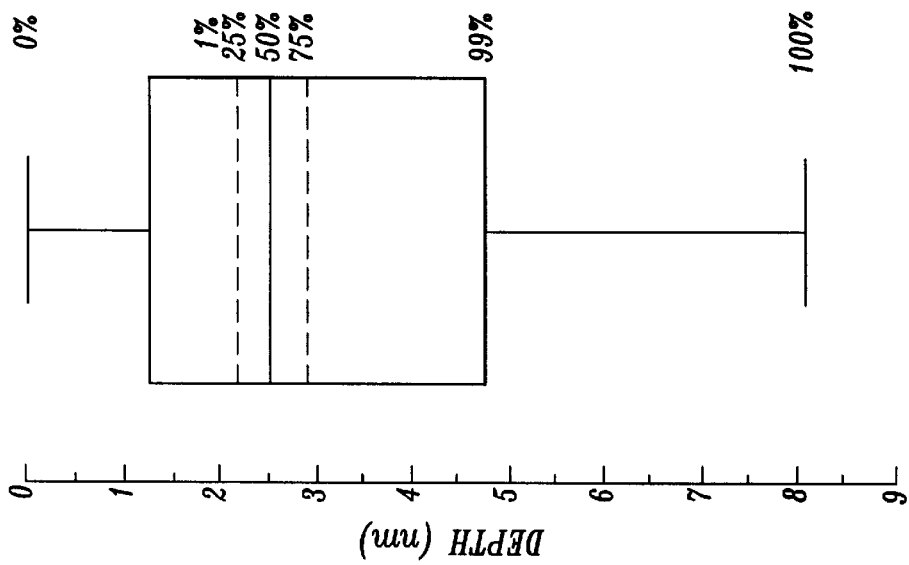
Fig. 4. 5 nm GOLD IMP
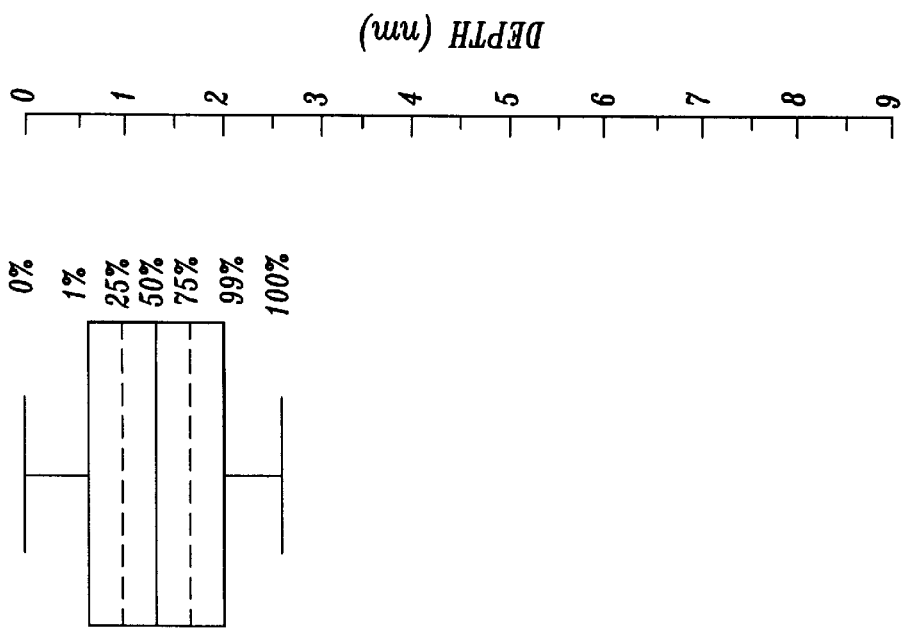
Fig. 3. CONTROL IMP

TEMPLATE IMPRINTED MATERIALS BY RFGD PLASMA DEPOSITION

This application claims benefit of priority from U.S. provisional patent application Ser. No. 60/82,150, filed on Apr. 17, 1998.

FIELD OF THE INVENTION

The present invention relates to structures having template-imprinted surfaces, and to methods for making template-imprinted structures.

BACKGROUND OF THE INVENTION

Materials capable of binding specific cells or molecules, especially macromolecules such as proteins, peptides and nucleic acids, play an important role in a wide range of biomedical applications that include molecular separation, biosensors, and medical devices.

For example, affinity chromatography exploits the recognition between an immobilized ligand and the protein to be separated. In biospecific affinity chromatography, monoclonal antibodies or enzyme substrates are covalently linked to an inert matrix to purify the proteins recognized by the antibodies, or the enzymes that bind to the substrates. Biomolecules are, however, labile and expensive, and often difficult to immobilize.

Biosensors combine a biological recognition mechanism with a physical transduction technique. They find various applications in medical diagnostics (in vitro and in vivo), environmental monitoring, and industrial processing. A biosensor usually utilizes biomolecules, such as antibodies or receptors, or biological systems, such as cells, as sensing elements for analytes. Again, the development of biosensors is largely impeded by problems with biological components, such as their inherent instability.

The clinical success of a medical prosthesis, that is inserted into a mammalian body, depends primarily on the ability of the surface of the prosthesis to promote or inhibit specific protein and cellular responses. When a medical prosthesis is placed into the body, proteins adsorb almost instantaneously onto the surface. The cellular responses of the body to the prosthesis are mediated by interactions between the adsorbed protein layer on the prosthesis surface and the protein receptors on cell surfaces. Thus, the composition and conformation of the adsorbed protein layer on the surface of a prosthesis is largely responsible for dictating the biological response to that surface. To avoid rejection of the implanted biomaterial, therefore, a precisely engineered surface with ordered recognition sites for specific proteins is required. Despite many attempts to produce materials that preferentially bind a specific protein from plasma, most existing biomaterials exhibit a nonspecific biological reaction, with a broad spectrum of active processes simultaneously occurring, which may lead to rejection of the implant. A new generation of biomaterials engineered for specific protein recognition is required.

Thus, there is a need for structures, such as medical prostheses and biosensors, having surfaces that are durable and are capable of specifically binding cells or molecules, particularly biological macromolecules such as proteins, peptides and nucleic acids. Further, there is a need for methods of making structures having surfaces that are capable of specifically binding cells or molecules, especially biological macromolecules.

SUMMARY OF THE INVENTION

The present invention provides structures having at least one template-imprinted surface defining indentations that are capable of specifically binding cells and/or molecules, such as macromolecules including proteins, peptides and nucleic acids. Presently preferred embodiments of the template-imprinted structures of the present invention include medical prostheses, such as artificial joints and heart valves, having surface indentations that specifically bind proteins and/or cells that enhance the biocompatibility of the prosthesis, thereby making it less likely that the prosthesis will be rejected by the body. Methods are also provided for making the template-imprinted structures of the present invention.

In one aspect, the present invention provides structures, such as medical prostheses and microchips, having at least one template-imprinted surface defining indentations, the template-imprinted surface includes a plasma-deposited layer and a sugar layer covering at least a portion of the plasma-deposited layer. The indentations are capable of specifically binding a macromolecule, such as proteins, peptides and nucleic acids. Preferably cells or macromolecules are bound to the portion of the sugar layer within the indentations by non-covalent interactions, such as hydrogen bonds and Van der Waals interactions. The sugar layer is preferably composed of trehalose, although other sugars, such as sucrose, lactose, mannose, maltose, fructose, glucose and galactose may be used to form the sugar layer. The template-imprinted surface is preferably affixed to the underlying structure, such as a medical prosthesis or microchip, by an adhesive, more preferably by an epoxy resin. In a presently preferred embodiment, the plasma-deposited layer is deposited by Radio Frequency Glow Discharge (R.F.G.D.), although other plasma deposition methods, such as, but not limited to, direct current glow discharge plasma deposition, pulsed glow discharge plasma deposition and microwave glow discharge plasma deposition may be used to form the template-imprinted structures of the present invention. The template-imprinted structures of the present invention may also include a plurality of templates, such as macromolecules or cells, disposed within the indentations and retained therein, preferably by non-covalent interactions between the templates and the hydroxyl groups of the sugar molecules of the sugar layer. When the template is a protein having an active site, the protein molecules are preferably disposed within the indentations so that the active site of a proportion, preferably substantially all, of the protein molecules is accessible to a binding ligand.

In another aspect, the present invention provides methods for forming a template-imprinted structure, the methods including the steps of (a) depositing a layer of sugar onto a first supporting surface bearing a plurality of templates; (b) forming a plasma-deposited layer by depositing plasma onto the sugar layer; (c) affixing the plasma-deposited layer to a second supporting surface (such as a surface of a medical prosthesis or microchip); and (d) removing the first supporting surface and the templates. The presently preferred first supporting surface is mica, but can also be any material which can be rendered ultrasmooth and/or ultraflat, for example glass or silicon wafer. The preferred templates are cells, proteins, peptides and nucleic acids, although the methods of the present invention can also be utilized to form imprints of other molecules, such as, but not limited to, drug molecules, hormones including steroids, pesticides, dyes and amino acids. The presently preferred sugar is trehalose, although other sugars can be used, such as sucrose, lactose, mannose, maltose, fructose, glucose and galactose, provided that the selected sugar is capable of preserving the stability of dried proteins thru hydrogen bonding. The presently preferred method of forming the plasma-deposited layer is Radio Frequency Glow Discharge (R.F.G.D.), although other plasma deposition techniques can be used, such as, but not limited to, direct current glow discharge plasma deposition, pulsed glow discharge plasma deposition and microwave glow discharge plasma deposition. Preferably, the plasma-deposited layer is affixed to the second supporting surface by an adhesive, more preferably by an epoxy resin.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 shows box plots of the surface height distribution of control poly-L-lysine treated mica.

FIG. 4 shows box plots of the surface height distribution of a 5 nm colloidal gold imprint.

DETAILED DESCRIPTION OF THE PREFERRED EMBODIMENT

As used herein, the term "template" refers to an object, the shape of at least a portion of which is imprinted onto a surface including an outer sugar layer and an underlying plasma-deposited layer. Template-imprinted structures of the present invention thus include a surface having indentations that are complementary in shape to at least a portion of a template used to form the indentations. By way of non-limiting example, presently preferred templates include cells, proteins, peptides, nucleic acids (such as oligonucleotides, cDNA molecules and genomic DNA fragments), hormones, drug molecules, pesticides, dyes, amino acids and colloidal gold particles.

In the practice of the present invention, structures are template-imprinted, on at least a portion of their surfaces, with cells or molecules, preferably macromolecules such as proteins and nucleic acids, so that the surface, template imprints are complementary to the shape of the portion of the template that formed the imprint. Thus, template-imprinted structures of the present invention can specifically bind the template cells or molecules that were used in the template- imprinting process. The methods of the present invention can be utilized to template-imprint the surface of a variety of structures including, but not limited to, medical prostheses (such as artificial heart valves, artificial limb joints, contact lenses and stents), microchips (preferably silicon-based microchips) and components of diagnostic equipment designed to detect specific microorganisms, such as viruses or bacteria. The template-imprinted structures of the present invention can be used, for example, to monitor the levels of specific chemical compounds or cells in a bioreactor or in contaminated groundwater.

Figure 1:
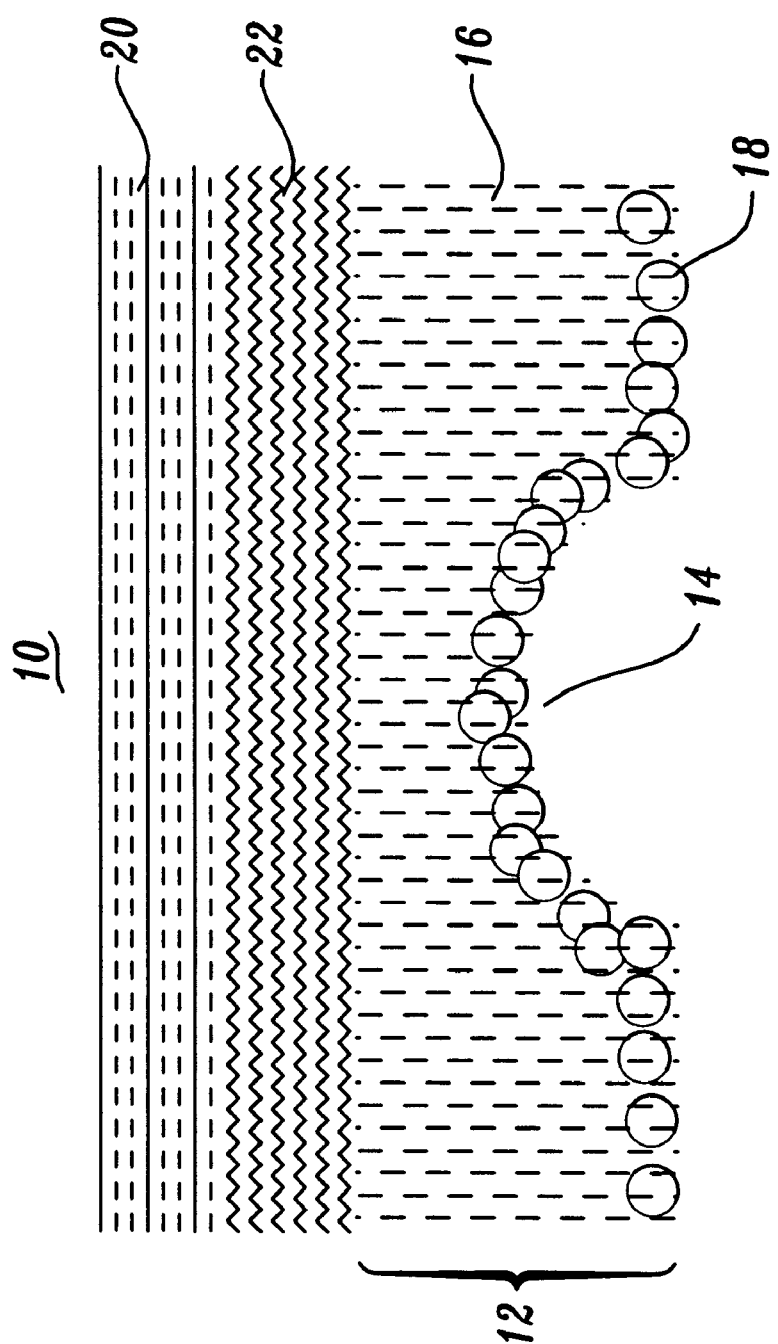
FIG. 1 shows a presently preferred embodiment of the template-imprinted structures of the present invention.

As shown in FIG. 1, in a presently preferred embodiment template-imprinted structures 10 of the present invention include a template-imprinted surface 12 defining indentations 14. Template-imprinted surface 12 includes a plasma-deposited layer 16 and a sugar layer 18 covering plasma-deposited layer 16. Template-imprinted surface 12 is preferably affixed to a supporting surface 20 with a layer of adhesive 22, preferably epoxy adhesive. Indentations 14 are capable of specifically binding templates, such as cells, proteins and nucleic acids, used to form indentations 14.

Figure 2:
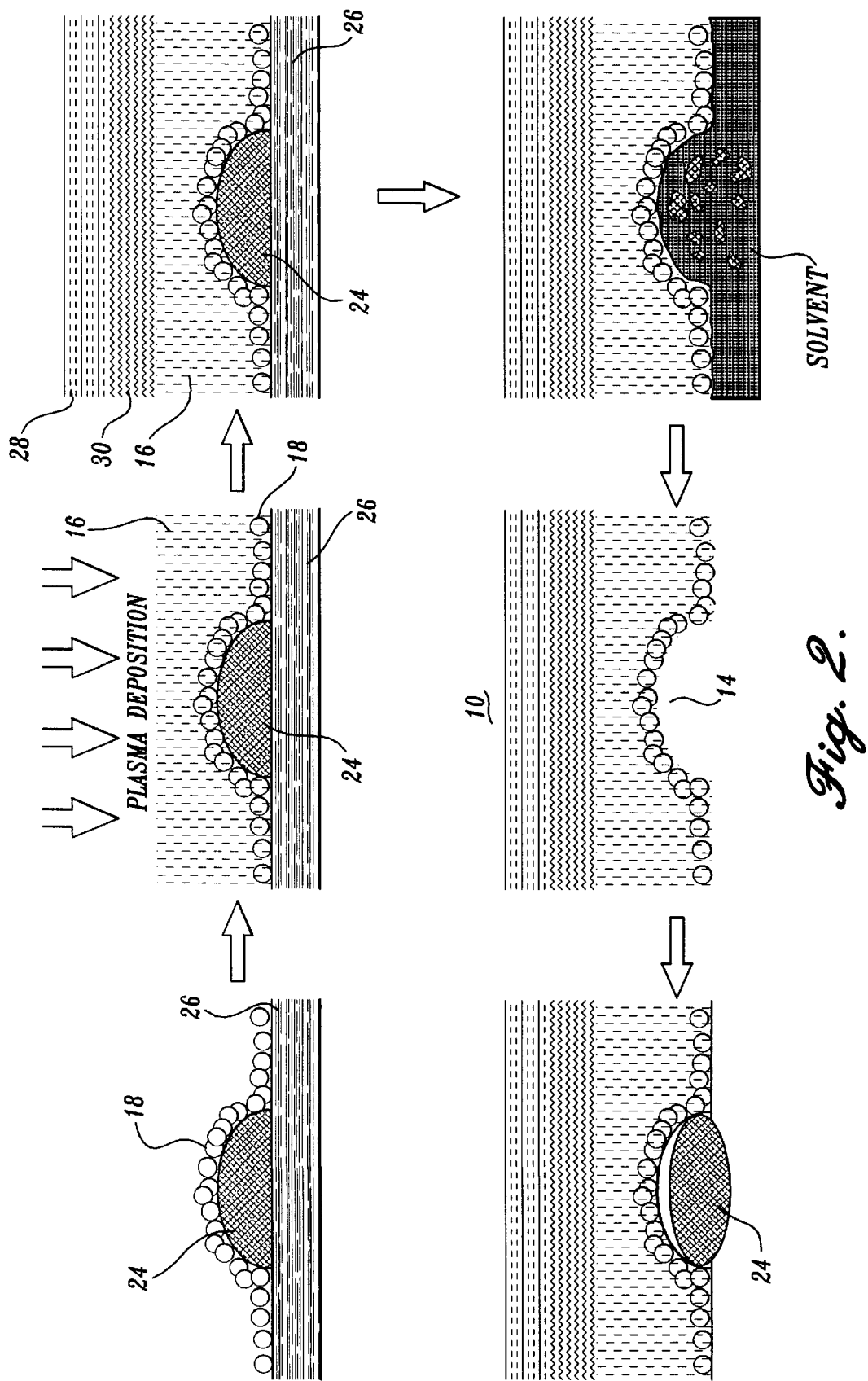
FIG. 2 shows a schematic representation of a presently preferred embodiment of a method of making the template-imprinted structures of the present invention.

As shown in FIG. 2, in the practice of the methods of the present invention, template-imprinted structures 10 are formed by absorbing template 24 onto first supporting surface 26, preferably made from freshly cleaved mica, and coating template 24 and first supporting surface 26 with sugar, preferably trehalose, to form sugar layer 18. Plasma is deposited over sugar layer 18 to form plasma-deposited layer 16 which is preferably affixed to a second supporting surface 28 with an adhesive layer 30, preferably a layer of epoxy resin. First supporting layer 26 and template 24 are then removed to expose indentation 14 that is complementary in shape to the portion of template 24 that was coated with sugar layer 18. Thus, indentation 14 is capable of specifically binding template 24 that was used to form indentation 14.

Mica is the presently preferred first supporting surface 26 for the adsorption of templates 24, such as proteins, because the surface of mica can be rendered atomically flat. Mica is a group of layered aluminosilicate minerals with the ideal structure of $KAl_2[AlSi_3O_{10}](OH,F)_2$. It has a complex multi-layered structure in which tetrahedral double sheets of $(Si,Al)_2O_5$ are electrostatically linked by a layer of hexagonally coordinated cations such as $K^+$. This layer is easily disrupted by cleavage, which exposes a basal plane covered by $K^+$. In air, this layer is completely neutralized by the negative aluminosilicate lattice charge, but in water some of the $K^+$ ions dissociate from the surface and result in a negative surface charge. Therefore, by using mica as first supporting surface 26, template-imprinted surface 12 will only bear the imprint of template 24. Moreover, the hydrophilic, negatively charged surface of mica minimizes denaturation of adsorbed proteins.

In addition to mica, first supporting surface 26 can also be made from other materials that can absorb cells and molecules, especially macromolecules. By way of non-limiting example, first supporting surface 26 can also be made from glass, thin hydrogel films (preferably having a thickness of from about 10 Å to about 1000 Å), plastics, such as polyethylene terephthalate (Pet), and metallic foils. First supporting surface 26 should be very smooth so that only the topography of the template is reflected in the replica imprints.

Templates 24 can be cells or molecules, in particular macromolecules such as proteins, peptides and nucleic acids. By way of non-limiting example, cells that can be utilized as templates 24, and which can therefore be specifically bound by template-imprinted structures 10 of the present invention, include keratinocytes and other epithelial cells, macrophages, platelets, T cells, B cells, polymorphonuclear (PMN) cells, neutrophils and other cells of hematopoietic origin, mast cells, Langerhans cells and other dendritic cells of tissue derivation, neurons, glial cells, astrocytes, fibroblasts, osteocytes, osteoclasts, endothelial cells, pericytes, smooth muscle cells, and microorganisms such as bacteria, fungi and viruses.

By way of non-limiting example, proteins and peptides that can be utilized as templates 24, and which can therefore be specifically bound by template-imprinted structures 10 of the present invention, include, but are not limited to, plasmin, plasminogen, tissue plasminogen activator, ceruloplasmin, fibronectin, vitronectin, thrombin and fibrinogen; growth factors and cytokines including but not limited to platelet derived growth factors (PDGF), angiogenin, angiostatin, fibroblast growth factors (FGF), keratinocyte growth factors (KGF), macrophage activating factors (MAF), interferons (IFN), interleukins (IL) lymphokines, transforming growth factors (TGF), bone morphogenic proteins (BMP) and chemokines; extracellular matrix and matricellular proteins including, but not limited to, collagens, laminins, osteopontins, thrombospondins, SPARC and osteonectins; proteoglycans and other tissue components, including but not limited to, hyaluronic acids, demosines, vimentins, glysoaminoglycans, actins and myosins; and other activators of the immune system including but not limited to antibodies and immunoglobulins of all types.

By way of non-limiting example, nucleic acids that can be utilized as templates 24, and which can therefore be specifically bound by template-imprinted structures 10 of the present invention, include RNA, including messenger RNA, transfer RNA and ribosomal RNA, and DNA, including cDNA, genomic DNA and oligonucleotide molecules.

Sugar layer 18 that is deposited on first supporting surface 26, bearing a plurality of templates 24, is preferably formed from trehalose. While not wishing to be bound by theory, it is believed that trehalose, a disaccharide ($C_{12}H_{22}O_{11}$) composed of 2 D-glucose molecules, forms hydrogen bonds with the surface residues of templates 24, such as proteins. The resulting "shell" of sugar thus prevents templates 24, such as proteins, from denaturation due to drying, and from structural degradation during the plasma-deposition step. Further, the portion of sugar layer 18 surrounding template 24 forms an indentation 14 having a shape that is complementary to the shape of template 24. In addition to trehalose, the sugar used to form sugar layer 18 can be sucrose, lactose, mannose, maltose, fructose, glucose and galactose. Additionally, sugar layer 18 can be formed from other chemicals that are capable of stabilizing the three dimensional structure of templates 24, and protecting templates 24 from dehydration and destruction during plasma deposition. By way of non-limiting example, sugar layer 18 can be formed from polyhydric alcohols such as mannitol, myoinositol, glycerol and polyethyleneglycol. The presently preferred method of forming sugar layer 18 is spin casting by which a 0.01 to 100 mM solution of sugar, preferably trehalose, is spin cast with a photoresist spinner at a spinning speed of 3000 to 5000 rpm for a period of about fifteen to thirty seconds. Additionally, sugar layer 18 can be formed, for example, by sol-gel spraying and dip-coating. A presently preferred thickness range for a sugar layer 18 formed from trehalose is from about 2 nm to about 8 nm.

Plasma-deposited layer 16 is formed by depositing plasma onto sugar layer 18. The term plasma refers to a gaseous, ionized state of matter containing ions, electron, free radicals and neutral species. Plasma can be generated by providing an input of excitation energy to gaseous molecules which results in their ionization. The preferred method of depositing plasma onto sugar layer 18 is Radio Frequency Glow Discharge (R.F.G.D.). Radio frequency glow discharge is commonly used for the generation and continuous maintenance of low temperature plasmas. When a RFGD glow discharge plasma is created using an organic vapor, deposition of a polymeric overlayer occurs on the exposed surface. Organic molecules on the surface can also be crosslinked and incorporated into the deposited films.

The mechanisms of plasma deposition are complex and involve reactions between plasma species, between plasma and surface species, and between surface species. Because there is sufficient energy from the plasma to rip apart any organic molecule, precursor molecules in the plasma can fragment at any point in their structure. The resulting reactive molecules can then recombine into new structures and deposit on the surface, or react with neutral molecules previously on the surface. The continual bombardment and adsorption of plasma species on the substrate surface results in a growing plasma film and leads to a highly crosslinked polymeric overlayer.

RFGD Plasma deposited films offer several unique advantages. They are smooth, conformal and uniform. Film thickness is easily controlled and ultrathin films (10–1000 Angstroms) are readily achieved, allowing for surface modification of a material without alteration to its bulk properties. Moreover, plasma films are highly-crosslinked and pin-hole free, and therefore chemically stable and mechanically durable. In addition, the processing is rapid and done dry, rendering good manufacturability. RFGD plasma deposition of organic thin films has been used in microelectronic fabrication, adhesion promotion, corrosion protection, permeation control, as well as biomaterials.

Fluorocarbon gases, such as hexafluoropropylene ($C_3F_6$, or $CF_3CFCF_2$) are preferably used in RFGD plasma deposition as precursors, because it has often been observed that RFGD plasma deposited fluoropolymers form ultrasmooth films with roughness comparable to that of mica. In addition, the deposited fluoropolymer films are mechanically stable and resistant to organic solvents such as ethanol or acetone. Routine optimization of the conditions of RFGD plasma deposition, such as RF power, gas flow rate, and the sample position, facilitates crosslinking the sugar molecules around templates 24, such as proteins, but keep the damage to templates 24 minimal. The presently preferred method of forming plasma-deposited layer 16 is Radio Frequency Glow Discharge (R.F.G.D.). Exemplary issued United States patents disclosing R.F.G.D. methods useful in the practice of the present invention include: U.S. patent Ser. No. 4,656,083; U.S. patent Ser. No. 5,034,265 and U.S. patent Ser. No. 5,153,072, each of which patents are incorporated herein by reference. R.F.G.D. methods useful in the practice of the present invention are also described in B. D. Ratner et al., "Plasma deposition and treatment for biomedical applications" in *Plasma Deposition, Treatment and Etching of Polymers* (Ed: R. d'Agostino), Academic, San Diego, 1990, pp 463–516; B. D. Ratner, "Ultrathin films (by plasma deposition)" In *Polymeric materials encyclopedia* (Ed: Salamone, J. C.) CRC, Boca Raton, 1996, each of which publications are incorporated herein by reference. Other plasma deposition techniques are useful in the practice of the present invention such as, but not limited to, direct current glow discharge plasma deposition, pulsed glow discharge plasma deposition and microwave glow discharge plasma deposition. Additionally, other vacuum deposition techniques, such as chemical vapor deposition, may be used to coat sugar layer 18.

Plasma-deposited layer 16 is affixed to second supporting surface 28, which is preferably the surface of a medical prosthesis or the surface of a microchip. Plasma-deposited layer 16 is preferably affixed to second supporting surface 28 by an adhesive, most preferably by an epoxy resin. Examples of epoxy resins that can be used to affix plasma-deposited layer 16 to second supporting surface 28 are Epo-Tek® 301 (Epoxy Technology, Billerica, Mass.), Epo-Tek® 715 (Epoxy Technology), EP30 (Master Bond, Hackensack, N.J.), EP21LV (Master Bond), Duro™ (Loctite, Hartford, Conn.). The presently preferred epoxy resin is EP21LV (Master Bond, Hackensack, N.J.). Another type of adhesive that can be used to affix plasma-deposited layer 16 to second supporting surface 28 are cyanoacrylate adhesives, such as Superbonder™ (Loctite).

After plasma-deposited layer 16 is affixed to second supporting surface 28, first supporting surface 26 and templates 24, such as proteins, are then removed. A presently preferred method of removing first supporting surface 26 is to peel it off. Templates 24 are then removed, for example with a solvent, more preferably with a detergent solution such as sodium hypochloride (NaClO), most preferably with a basic detergent solution (e.g., a mixture of NaOH and NaClO) which causes the partial decomposition of templates 24. Removal of first supporting layer 26 and templates 24 exposes indentations 14 in template-imprinted surface 12. Indentations 14 have a shape that is complementary to the portion of template 24 that was embedded in sugar layer 18, and are therefore capable of specifically binding template 24 that was used to create indentations 14 in template-imprinted surface 12. While not wishing to be bound by theory, it is believed that the portion of sugar layer 18 within indentations 14 has precisely positioned hydroxyl groups that form a pattern of non-covalent interactions with template 24, thereby facilitating the specific binding of template 24 that was used to create indentations 14.

Utilizing the methods of the present invention, a high imprinting fidelity of 10 nm or less can be achieved. As shown in Example 7, for example, the surface-imprinted structures of the present invention can specifically bind and differentiate between similar proteins with angstrom-order structural differences.

The following examples merely illustrate the best mode now contemplated for practicing the invention, but should not be construed to limit the invention.

EXAMPLE 1

Preparation of the First Supporting Surface

The following templates 24 were deposited on first supporting surfaces 26 made from mica: *E. coli* cells; proteins and colloidal gold particles. A control first supporting surface 26 was coated with poly-L-lysine.

To prepare the control, first supporting surface 26, a 100 mg/mL poly-L-lysine (Sigma, St. Louis, Mo.) solution was spin cast on a photolithography micro-fabricated silicon wafer (obtained from Sho H. Fuji at the Washington Technology Center) with a photo resist spinner (Headway Research, Garland, Tex.). The sample was then blown dry with a stream of pure $N_2$.

To prepare a first supporting surface 26 bearing *E. coli* cells as templates, *E. coli* (CD29, obtained from Jess A. Vasina at Chemical Engineering) cells in culture medium were deposited on freshly cleaved mica, incubated for 1 h, followed by a distilled water rinse and an N2 blowing dry.

To prepare a first supporting surface 26 bearing colloidal gold particles as templates, 100 µg/mL poly-L-lysine was spin cast on freshly cleaved muscovite mica (Ted Pella, Redding, Calif.), and dried with a stream of $N_2$. Colloidal gold particles of 20.5 nm (Coefficient of Variation<12%, ICN, Costa Mesa, Calif.), 9.8 nm (CV<12%, Sigma) and 5.2 nm (CV<15%, ICN) were then deposited on the poly-L-lysine treated or $MgCl_2$ treated mica, respectively. The samples were incubated for 5 min, followed by a distilled water rinse and were blown dry with an $N_2$ stream.

To prepare a first supporting surface 26 bearing proteins as templates 24, bovine fibrinogen (Fbgn) (Catalogue number F8630, Sigma), bovine Immunoglobulin G (IgG) (Catalogue number 641401, ICN), bovine serum albumin (BSA) (Catalogue number 820471, ICN), Chicken lysozyme (LSZ) (Catalogue number L6876, Sigma) and bovine ribonuclease (RNase) (Catalogue number R5250, Sigma) were used as templates 24 without further purification. Proteins were adsorbed on freshly cleaved mica in 0.2 mg/mL CPBS buffer (0.01 M sodium citrate, 0.01 M sodium phosphate and 0.12 M sodium chloride, pH 7.4). Following a 2 h adsorption at 37° C., the samples were rinsed by the dilution-displacement method with CPBS followed by distilled water. A trehalose (Sigma) solution of 100 µM was then spin cast on the samples.

EXAMPLE 2

Plasma Deposition

First supporting surfaces 26 prepared as set forth in Example 1 were coated with plasma in the following manner. Plasma deposition of fluoropolymers was conducted in an RFGD system. A tubular glass reactor (10 cm ID) was capacitively coupled to a 13.56 MHz radio frequency (RF) generator (Model HF-650, E.N.I. Power Systems Inc., Rochester, N.Y.) via a home-made matching network and two external, symmetrical, brass capacitor rings (1 in. width). Capacitors were typically separated by 8 inches. The vacuum system was pumped downed by a Stokes rotary vane pump (Model V-009-2, Stokes-Penwalt, Philadelphia, Pa.). Flow of the monomer gas, hexafluoropropylene ($C_3F_6$) (PCR, Gainesville, Fla.), was controlled by a mass flow controller (Model 80-4, Vacuum General, San Diego, Calif.). System pressure was maintained by a motorized throttle valve (model MDV-015, Vacuum General) connected to a capacitance manometer (model CML, Vacuum General) in a feedback loop. Samples were put on a glass rack which was placed in the "in-glow" region, the zone between the capacitor rings. The reactor chamber was evacuated to less than 10 mtorr and the $C_3F_6$ gas was introduced at a flow rate of 2 std $cm^3$/min. The plasma was generated at 20 W power for 5 min while the system pressure was maintained at 150 mtorr. After termination of the plasma reaction, the chamber was re-evacuated and brought to atmospheric pressure with air.

EXAMPLE 3

Surface Imprint Preparation

Plasma-deposited layers 16 prepared as described in Example 2 were glued to a second supporting surface 28 using an epoxy glue (EP21LV, Master Bond, Hackensack, N.J.). Second supporting surface 28 was a φ12 mm cover-glass (Deckglaser, Germany) for the imprints of proteins, *E. coli* cells and colloidal gold particles. As to the micromachined silicon wafer, second supporting surface 28 was a φ0 mm thin metal disk (Ted Pella). The epoxy on the sample was cured at 37° C. in oven for 12 h. Then the mica first supporting layer 26 was carefully detached from sugar layer 18 with tweezers or an adhesive tape. The metal disk was physically removed from the silicon wafer without further treatment.

For the imprints of *E. coli* cells and proteins, the glass coverslip was then soaked in an NaOH/NaClO (0.5/1.0%) solution for 30 min to 2 h, followed by a distilled water rinse and air dry. With the colloidal gold imprints, the glass coverslip was rinsed in a 1.0% NaClO solution prior to the water rinse and air dry. Each batch of protein imprints were prepared along with a control, non-protein imprint, which did not use any protein as template 24. Double-sided samples that had both sides glued with plasma films were made for radiolabeled protein adsorption studies, while the single-sided samples were prepared for surface characterization.

Unless stated otherwise, the following techniques were used (as described in the following examples) to characterize the properties of the template-imprinted surfaces 12 prepared as described in Examples 1–3.

Light Microscopy (LM)

Optical micrographs were taken by an Olympus Bx60 system (reflection) microscope (Olympus Optical, Tokyo, Japan) with an attached video camera.

Scanning electron microscopy (SEM)

SEM experiments were carried out using a JSM-6300F (JOEL USA, Peabody, Mass.) field emission scanning electron microscope. The imaging was performed at 10 kV with magnifications of up to 20,000X.

Scanning probe microscopy (SPM) and image analysis

Atomic force microscopy (AFM) images were acquired in ambient air with a Nanoscope III system (Digital Instruments, Saint Barbara, Calif.) operating in tapping mode, or a Nanoscope II system (Digital) operating in contact mode. For tapping mode imaging, the cantilevers were etched silicon (TESP, Digital Instruments) with oscillation frequency of 250–270 kHz. Nominal tip radius of curvature was claimed by the manufacturer to be 5–10 nm. The operating set point was approximately 70% of the free-oscillation amplitude and scan rates were between 0.5 and 2 Hz. For contact mode AFM imaging, silicon nitride cantilevers (NP, Digital) with a spring constant of 0.24–0.56 N/m were used. The tip radius was typically 15–50 nm. Scan rate was 1–2 Hz. All the images were captured in height mode (palette of color represents height; dark for low, light for high) and were flattened. Further image analysis included roughness, section, bearing, fractal, power spectral density (PSD), and autocovariance function (ACVF), all of which were performed with AFM built-in functions. Prior to the post-imaging analysis, images were planefitted to remove the sample tilt.

Electron spectroscopy for chemical analysis (ESCA)

ESCA analyses were performed on a SSX-100 spectrometer (Surface Science Instruments, Mountain View, Calif.) using a monochromatic Al Ka source, a detection system with a 30° solid angle acceptance lens, a hemispherical analyzer, and a multichannel detector. A low-energy (~5 eV) electron gun was used for charge neutralization on the non-conductive samples. Survey scans (0–1000 eV) were performed at a 150 eV analyzer pass energy using a 1000 $\mu$m X-ray spot size to determine elemental composition. High-resolution spectra were obtained using an analyzer pass energy of 50 eV. Angle-dependent XPS data were collected at nominal photoelectron take-off angle of 0°, 55° and 80°. The take-off angle was defined as the angle between the surface normal and the axis of the analyzer lens system. High-resolution spectra were resolved into individual Gaussian peaks using a least-squares fitting program. All binding energies (BE) scales were referenced by setting the $CF_2$ peak maxima in the C1s spectra to 292.0 eV.

Time-of-flight secondary ion mass spectrometry (ToF-SIMS)

The ToF-SIMS data were acquired using a Model 7200 Physical Electronics Instrument (PHI, Eden Prairie, Minn.). The 8 keV $Cs^+$ ion source was operated at a current of 1.5 pA and a pulse width of 0.9 ns. The total ion dose used to acquire each spectra was less than $2 \times 10^{12}$ ion/$cm^2$. The area of analysis for each spectrum was 0.01 $mm^2$. A low-energy electron gun was used for charge neutralization on the surfaces. Data were acquired over a mass range from m/z=0 to 2000 for both positive and negative secondary ions. The mass scale for the positive secondary ions was calibrated using the $CH_3$, $C_2H_3$ and $C_3H_5$ peaks.

Contact angle

Static advancing contact angles of water in air were obtained using a goniometer (A-100, Rame-Hart, Mountain Lakes, N.J.). A minimum of three spots were measured per surface tested.

Protein radiolabeling

Bovine IgG, fibrinogen, and BSA were radiolabeled with $^{125}I$ (Na $^{125}I$, Amersharn, Arlington Heights, Ill.) by the iodine monochloride (ICl) technique of MacFarlane[183] as modified by Horbett[184]. Molar ratio of ICl to protein was 1:1 for fibrinogen, 2:1 for BSA, and 1:1 for IgG, 1:1 for ribonuclease A and 1:1 for lysozyme. The unincorporated $^{125}I$ was separated from labeled protein using a Biogel P-4 column (Bio-Rad, Richmond, Calif.). The labeled proteins were dialyzed overnight against CPBS with the addition of 0.02% sodium azide. The solution concentrations of the iodinated protein were determined using the absorbence at 280 nm of appropriately diluted samples. The extinction coefficients for the bovine proteins were 1.5 OD/mg/mL for bovine fibrinogen, 1.38 OD/mg/mL for bovine IgG, 0.6 OD/mg/mL for BSA, 2.6 OD/mg/mL for chicken lysozyme, and 0.7 OD/mg/mL for bovine ribonuclease A. Radiolabeled protein solutions were stored at −70° C. and used within 2 weeks of preparation.

Protein adsorption from single solutions and detergent elution

Samples were placed in 2 mL polystyrene cups (Evergreen Scientific, Los Angeles, Calif.) containing 1 mL degassed, fresh PBS buffer. A small amount of $^{125}I$-labeled stock protein solution was added to the unlabeled protein solution to obtain a 2× protein solution with specific activity of $10^6$–$10^7$ cpm/mg. Protein adsorption was then initiated by pipetting 1 mL 2X "hot" protein solution to the sample immersed in buffer to achieve a final 1X concentration. Complete mixing was achieved by gently repipetting. Adsorption was conducted for 2 h at 37° C. and terminated by dilution-displacement of the protein solution with buffer. The dilution-displacement technique was performed by flowing approximately 20 volumes of CPBS buffer at a flow rate of 400–600 mL/min through the cup. The protein solution was thus rapidly displaced, and exposure of the sample to an air-water interface was avoided. Following protein adsorption and sample rinsing, samples were placed in sample-counting tubes with 2 mL of a 3% SDS solution or a 0.5% Tween-20 solution. Sample radioactivity was then measured using a $\gamma$-counting system (Model 1185R, TM Analytic, Elk Grove, Ill.), followed by correction for decay and background. The amount of adsorbed protein was calculated from the radioactivity, the specific activity of the adsorbing solution, and the planar surface area of the sample. After 24 h of SDS or Tween-20 elution, samples were serially dip-rinsed in CPBS buffer and put in sample-counting tubes for measurement of radioactivity. The amount of protein remaining on the surface following elution was calculated for each sample.

Competitive protein adsorption from binary mixtures

Competitive adsorption studies were performed using binary mixtures of BSA and IgG, and LSZ and RNase. The $^{125}I$-labeled stock protein was added to a solution of the same protein solution to achieve a solution with specific specificity of $10^7$ cpm/mg and a concentration 4X the desired final concentration (0.01 mg/mL). A series of solutions of unlabeled, competitor protein were prepared in multiples of the labeled protein concentration as follows: 0.001, 0.01, 0.1, 1.0, 10, 100, and 1000. A series of binary mixtures were then prepared by mixing equal volumes of the radiolabeled protein solution and the unlabeled competitor protein solution to achieve a series of 2X binary solutions. The remainder of the adsorption process was the same as described in the preceding section. The amount of labeled protein adsorbed on each surface as a function of unlabeled protein/labeled protein concentration ratio [0.001, 0.01, 0.1, 1.0, 10, 100, and 1000] was determined.

Plot analysis of competitive adsorption data

Plots of adsorption of labeled protein vs. ratio of unlabeled protein/labeled protein were generated. They appeared to have the previously reported sigmoidal shape when the X axis was plotted on a log scale. Kaleidagraph™ software (Synergy, Reading, Pa.) was used to fit the curve to an equation given by Eq. (1) as previously described. $A_b$ is the amount of protein adsorbed (ng/cm$^2$), $A_{bmax}$, is the maximum amount of adsorbed protein (ng/cm2), A is a constant, and $R_{50}$ is the protein concentration ratio causing a 50% adsorption reduction in the maximum adsorption of the labeled protein. Kaleidagraph™ uses the chi-square criteria for estimating the best fit with a Levenberg-Marquardt iterative non-linear least squares algorithm. Fitted values for $R_{50}$ and $A_{bmax}$ as well as goodness of fit statistics were determined for each binary mixture pair on each sample.

$$A_b = A_{bmax} \cdot C/(C+1/R_{50})$$

EXAMPLE 4

Imprinting Fidelity of RFGD Plasma Deposition at the Micron Scale

To assess the imprinting fidelity of RFGD plasma deposition on the micron scale, a micromachined silicon wafer, fabricated by photolithography, was utilized as a first supporting surface 26. The silicon wafer bore 2–10 μm surface features including lines, circles and squares. A fluoropolymer imprint of the patterned silicon surface was prepared by plasma deposition of $C_3F_6$ and gluing of the plasma film to a second supporting surface 28, followed by stripping of the silicon wafer. A dilute poly-L-lysine solution was spin cast on the silicon wafer surface as a mold release agent before plasma deposition, because the plasma film would otherwise adhere to the silicon wafer tenaciously.

Reflection light microscopy pictures of the microfabricated silicon wafer and its fluoropolymer imprint demonstrated that the imprint corresponded very well in lateral dimensions to the template. Contact AFM imaging revealed sharp-cornered square indentations measuring 2 μm in width and 0.42 μm in depth.

EXAMPLE 5

Imprinting Fidelity of RFGD Plasma Deposition at the Nanometer Scale

Monodisperse colloidal gold particles of 20, 10 and 5 nm diameter were template-imprinted, because of their narrow size distribution and the ease of template preparation. The colloidal gold particles were deposited on poly-L-lysine treated mica. Following plasma deposition, attachment of plasma layer 16 to a second supporting surface 28, and removal of the mica, the exposed imprint surface was rinsed with NaClO to remove the embedded gold particles.

The contact AFM image of a 20 nm colloidal gold imprint showed that many pproximately 20 nm sized indentations 14, and some 40–60 nm indentations 14, existed on the surface. Indentations 14 were clearly seen to be close to 20 nm in diameter. Bright dots were observed that were perhaps partially-embedded gold particles which had not been washed away by NaClO. The depth of indentations 14 was found to be 6–8 nm and the big indentations 14 were close to 20 nm deep. The small indentations 14 were thought to be the imprints of single gold particles. Their shallower-than-expected depth was because the relatively large tip used in contact AFM, 15–50 nm for tip curvature radius, cannot probe down to the bottom of indentations 14 to interpret the depth correctly. The larger indentations 14 are perhaps the imprints of the 2-D clusters of gold particles, whose existence is confirmed by AFM imaging of 20 nm gold colloid particles on poly-L-lysine treated mica (data not shown). These large indentations 14 allowed the tip to probe down to the bottom.

The imprints of 10 nm and 5 nm colloidal gold particles were imaged by a Tapping Mode AFM, since the smaller radius of its etched silicon tip, 5–10 nm, may be able to resolve the sub-20 nm indentations 14. The template-imprinted surface 12 of 10 nm colloidal gold deposited on poly-L-lysine treated mica was observed to have many indentations 14, as well as some partially embedded nanogold particles. The diameter of indentations 14 was around 10 nm, while the depth of indentations 14 was in the range of 1.2–2.5 nm.

Contact AFM imaging of 5 nm colloidal gold particles deposited on mica revealed many approximately 30 nm dots, and some 50–90 nm dots, on the surface. The former are believed to be the single 5 nm colloidal gold particles, which were laterally enlarged because of the tip convolution; the latter are probably the 2-D clusters of closely packed colloidal particles, since the heights of both small and big dots are around 5 nm, as indicated by cross section profile analysis. On the template-imprinted surface 12, some big indentations 14 ranging from 10 to 90 nm in diameter were seen. These could be the imprint of the 2-D clusters of colloidal gold particles.

Since the imprint of a single 5 nm colloid particle was hardly visible because of the tip convolution, various AFM built-in statistical methods were employed to analyze the images of 5 nm gold template-imprinted surfaces 12, so as to extract quantitative information on surface roughness, texture, and features. Poly-L-lysine treated mica was used again for the deposition of 5 nm colloidal gold for the ease of template release. Imprints of mica treated with poly-L-lysine only were prepared as control surfaces. Three different spots of each triplicate sample were imaged, and altogether nine images of 3×3 μm were obtained.

RMS roughness ($R_q$) and mean roughness ($R_a$) for the imprint (Au IMP) and control surfaces (control IMP) are measured as shown in Table I. $R_q$ is the standard deviation of height over the template-imprinted surface 12. It describes the spread of the height distribution about the mean value. $R_a$ gives the mean value of the surface relative to the center plane, which divides the image surface equally[191]. Imprinting with 5 nm colloidal gold gives rise to substantially rougher surfaces than the control.

Autocovariance analysis of the AFM runs a statistical covariance of the image data, yielding an image which highlights inherent, periodic features. Covariance, the peak value of the calculated autocovariance function, could be related to the average size of certain "hidden" surface features. The averaged covariance values for the images of 5 nm gold template-imprinted surfaces 12 and the controls are reported in Table I.

TABLE I

Surface Roughness and Autocovariance Results of 5 nm Nanogold Template-Imprinted Surfaces and Control (n = 9)

| Surface | Roughness | | Autocovariance |
|---|---|---|---|
| | Rq ± SEM (nm) | Ra ± SEM (nm) | Covariance ± SEM (nm$^2$) |
| 5 nm Au IMP | 0.72 ± 0.21 | 0.52 ± 0.13 | 0.43 ± 0.10 |
| Control IMP | 0.39 ± 0.12 | 0.28 ± 0.09 | 0.08 ± 0.03 |

Colloid template-imprinted surfaces 12 are shown to have a much larger covariance value than the control surfaces, suggesting a corrugated surface from the nanogold indentations 14.

Bearing analysis was used to determine the height distribution of a 5 nm gold template-imprinted surface 12 and its control imprint of poly-L-lysine treated mica over their surfaces. The depth values for the bearing ratio levels of 0, 1, 25, 50, 75 and 99% were plotted as a box plot for each image. The representative box plot of the surface height distribution for the control mica imprint is shown in FIG. 3. The depth values for the bearing ratio levels of 0, 1, 25, 50, 75 and 99% were plotted as a box plot for each image, and the complementary percentiles, i.e., 1% and 99%; 25% and 75%, were almost equally spaced from the median depth (50%), indicating a symmetric distribution of its surface height. The range between the minimum (0%) and the maximum depth (100%) was less than 3 nm, demonstrating a highly smooth surface. The 25% and 75% depth for the nanogold template-imprinted surface (shown in FIG. 4) were also spaced evenly apart from the median depth, suggesting the smoothness of the surface area where no nanogold particle were imprinted. The 99% depth, nonetheless, is much farther from the median than the 1% depth. This observation means the surface height distribution is slightly skewed to the deeper depth, indicating the existence of indentations 14 below the mean surface. The distance between the median surface plane (50%) and the lowest point (100%) is 5.5 nm, which suggests that indentations 14 are from the imprinting of 5 nm colloidal gold particles. The distance between the median (50%) and the highest point (0%) is 2.56 nm for the nanogold template-imprinted surface 12, considerably larger than that for the control, 1.54 nm. It is possibly due to the colloidal gold particles protruding above template-imprinted surface 12.

EXAMPLE 6

Template Imprinting of E. coli cells

Figure 5:
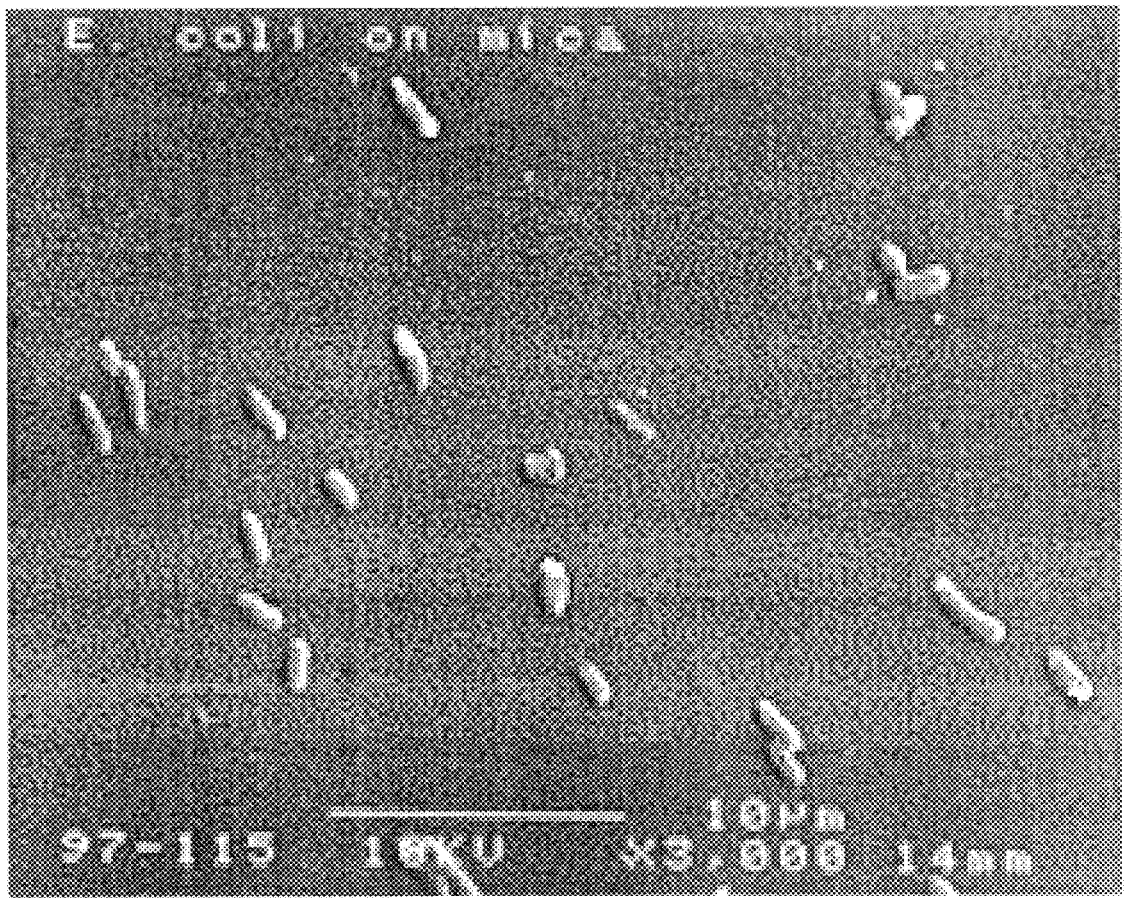
FIG. 5 shows an SEM micrograph of unfixed *E. coli* cells on mica.
Figure 6:
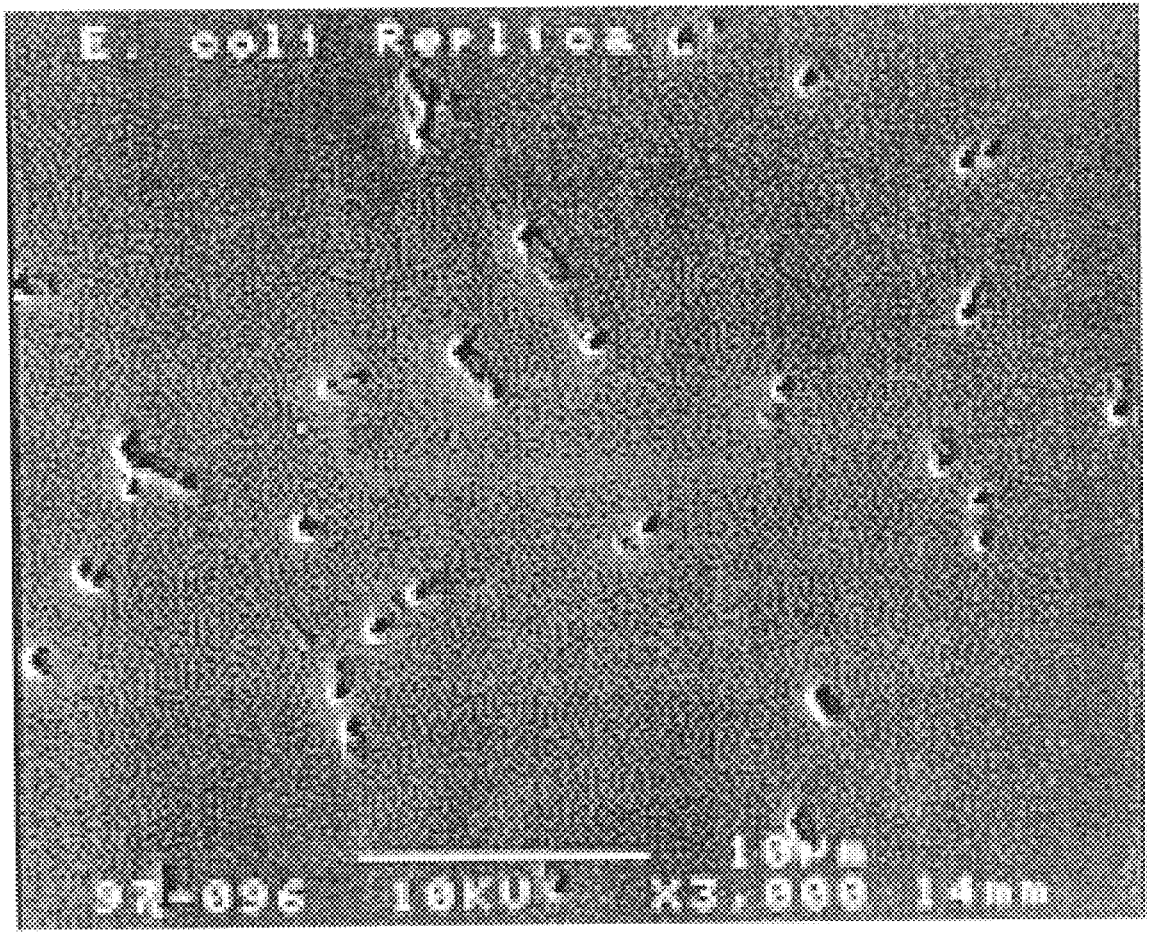
FIG. 6 shows an SEM micrograph of template-imprinted *E. coli* cells.

The ability to template imprint cells may have applications in biosensors and medical diagnostics. E. coli was selected for template imprinting because of its distinctive cylindrical shape and the micron-scale size. E. coli cells deposited on mica were template-imprinted by plasma deposition. After gluing plasma layer 16 to a second supporting surface 28 and then stripping the mica, the exposed, template-imprinted surface 12 was washed with NaClO and NaOH to remove the embedded E. coli. SEM micrographs show that unfixed E. coli cells on mica (FIG. 5) exhibit a similar size and shape. The neighboring paired cells are perhaps the cells in the stage of division. Cylindrical shaped indentations 14 are observed on the E. coli template-imprinted surface 12 (FIG. 6). Many of them seem to have a deep dent on one or both ends. The contact AFM image of a single E. coli cell on mica revealed the existence of a protrusion with its height of 275 nm at one end of the cell. This protrusion is presumably the protein/nucleotide rich region following the dehydration-induced collapse of the cell wall. The imprint of a single cell, as imaged by AFM, showed a corresponding dent of 350 nm deep at one end of the cylindrical cavity.

EXAMPLE 7

Template Imprinting of Proteins

In the presence of trehalose, three blood plasma proteins, IgG, albumin and fibrinogen, were imprinted because of their important roles in mediating cellular responses to blood contacting materials. Controls were prepared by imprinting mica coated with trehalose only.

IgG is the major antibody molecule of immune responses. It is made up of two identical "$F_{ab}$" arms and an "$F_c$" arm arranged in a "Y" shape, with a molecular weight of 150 kD. The length and width for each arm are 8.5 and 6 nm, respectively. Albumin contributes significantly to the osmotic blood pressure and aids in ligand transport and metabolism. It is a single polypeptide chain of 584 amino acids with a molecular weight of 69 kD. The molecular shape can be taken as an ellipsoid with dimensions of 4×14 nm. Fibrinogen plays an essential role in the hemostasis which involves blood coagulation and platelet aggregation. Human fibrinogen is a dimer of molecular weight of 341 kD. It is shaped as a tri-nodular rod with 45 nm in length and 6.5 nm in diameter.

Figure 7:
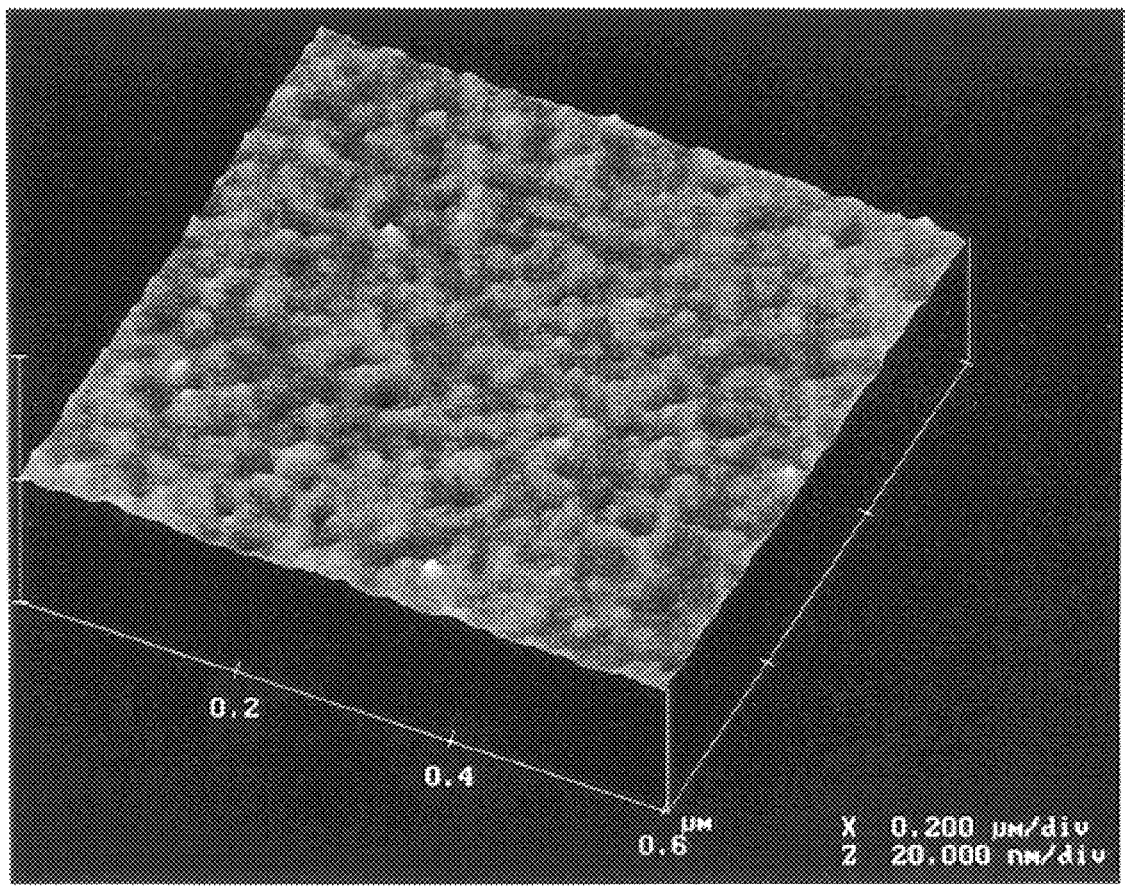
FIG. 7 shows a tapping mode AFM image of a control mica surface before elution with basic NaClO.
Figure 8:
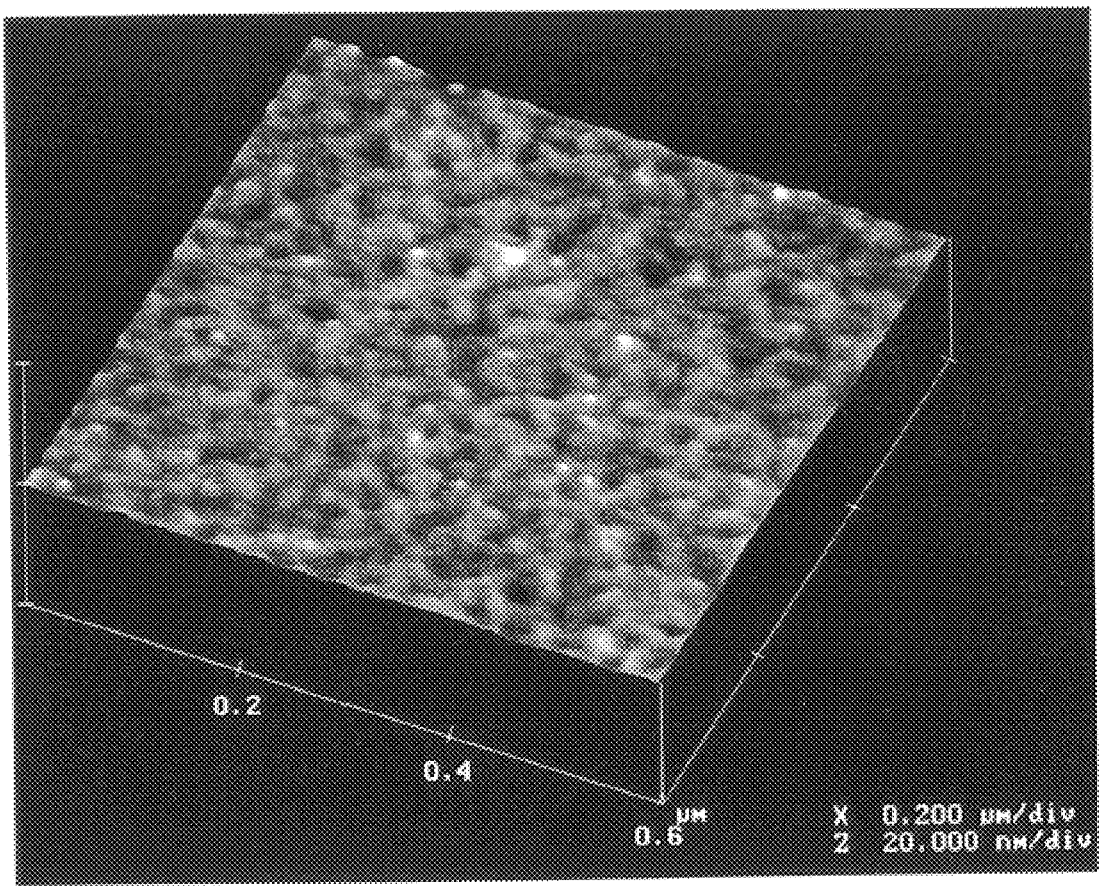
FIG. 8 shows a tapping mode AFM image of a control mica surface after elution with basic NaClO.
Figure 9:
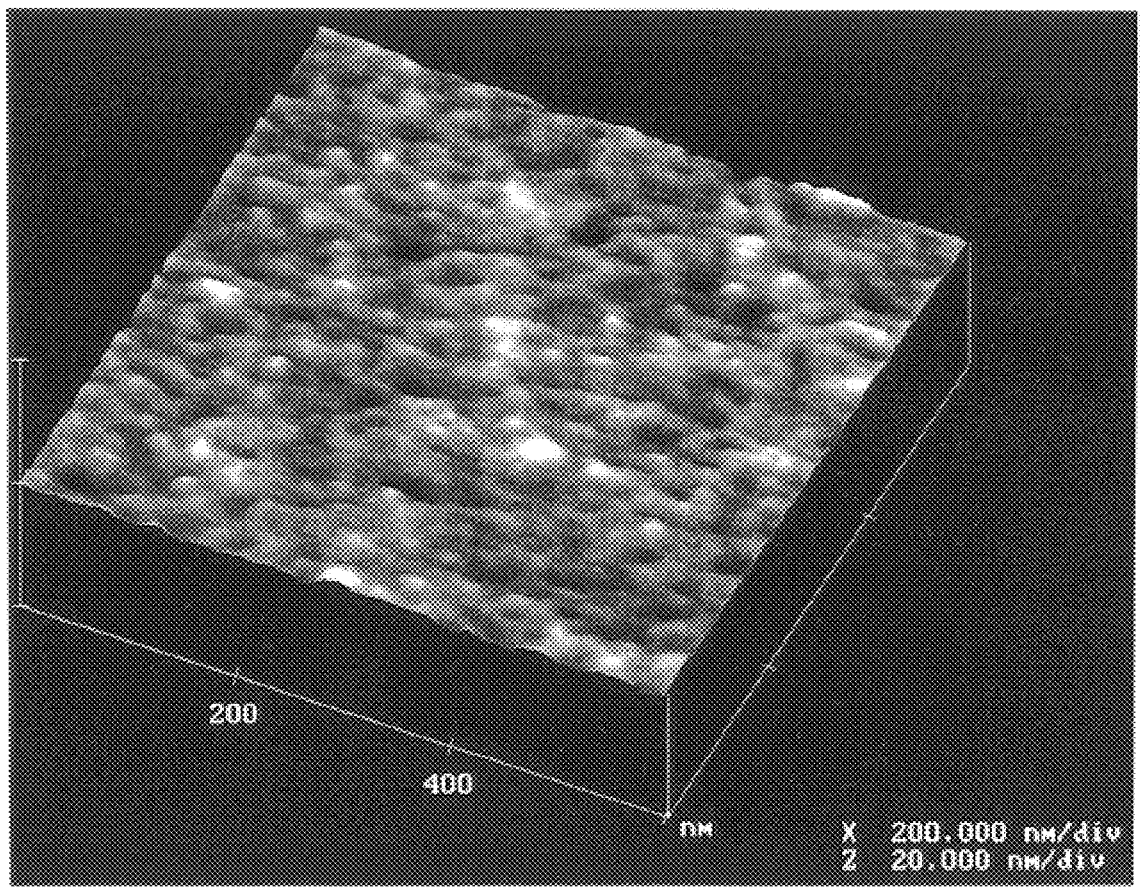
FIG. 9 shows a tapping mode AFM image of an IgG template-imprinted surface prior to elution with basic NaClO.
Figure 10:
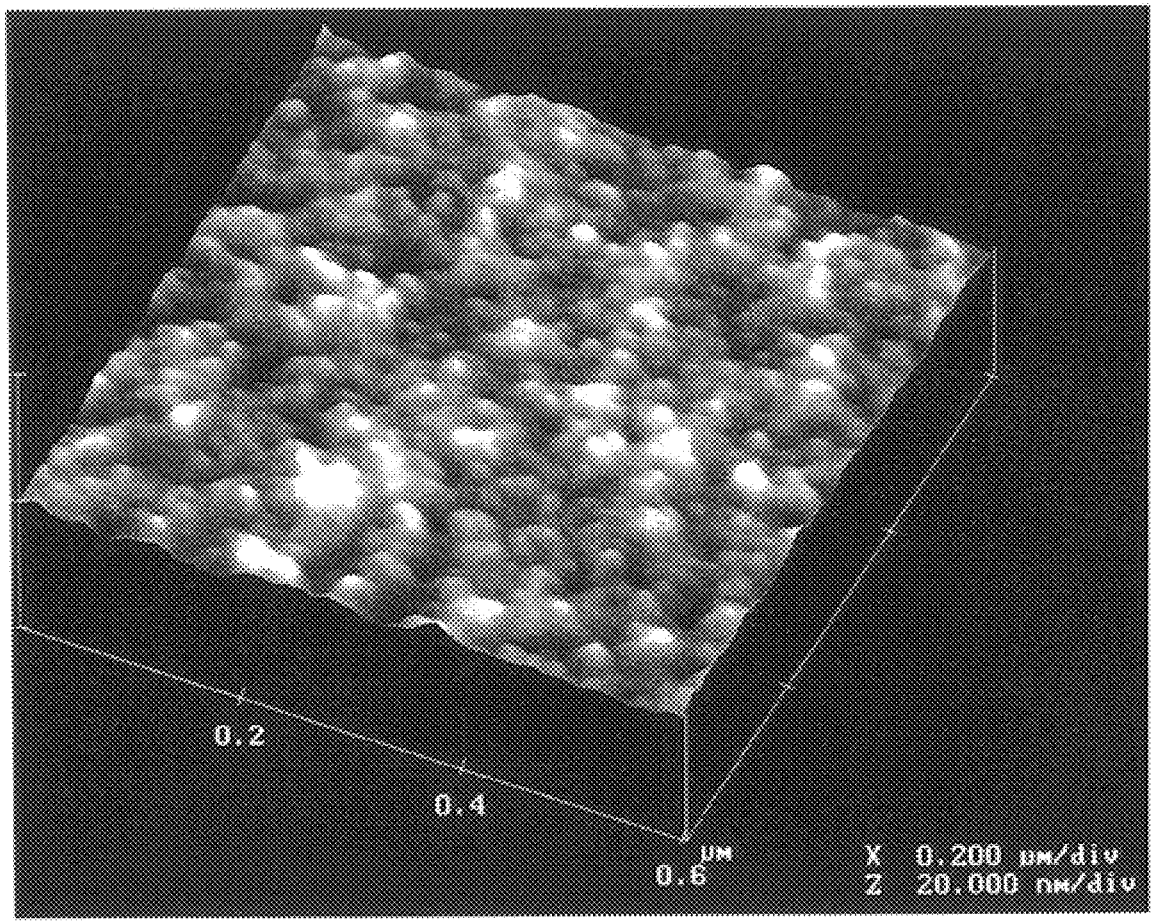
FIG. 10 shows a tapping mode AFM image of an IgG template-imprinted surface after elution with basic NaClO.

FIG. 7 and FIG. 8 show the tapping mode AFM images of non-protein imprinted control surfaces 12 (sugar imprinted surfaces), prior to and following the NaClO/NaOH elution, respectively. Both surfaces 12 seem to be smooth in the 20 nm Z range. Their resemblance in surface texture suggests that NaClO/NaOH treatment does not cause detectable surface erosion of the fluoropolymer plasma film or the crosslinked trehalose. Similarly, as shown in FIG. 9, IgG template-imprinted surface 12 prior to elution was found to be relatively smooth with a few shallow indentations 14 of 20–40 nm in diameter, which could be due to the IgG aggregates detached from surface 12 in the peeling of mica, since adsorbed IgG protein is observed to form agglomerates on mica under our experimental conditions (data not shown). As shown in FIG. 10, following elution IgG template-imprinted surface 12 became much rougher, and many peaks and valleys of varying sizes from 10 to 60 nm appeared over surface 12. This drastic change of surface morphology is because the elution oxidants such as NaOH partially decompose the surface-embedded protein into amino acids, so that the protein is easily washed off the imprint surface 12.

The tapping AFM image of the albumin imprinted surface 12 prior to elution also showed a very smooth surface, which could be the closely packed albumin molecules still trapped within indentations 14, since albumin readily forms a dense protein layer when adsorbed on mica (data not shown). The albumin imprinted surface 12 following elution, on the contrary, has many densely distributed peaks and indentations 14 of ~10 nm. Visible changes of surface texture is most prominent with the fibrinogen imprinted surface 12 prior to and after elution. The imprinted surface 12 without elution had many indentations 14, some of which are slightly elongated, over the surface. It is because some fibrinogen molecules adsorb to mica so firmly that they stay on the mica surface when mica is stripped off imprinted surface 12. This possibility seems highly likely for fibrinogen, which is known as a "sticky" protein. Many more trench-shaped indentations 14, of length 20–80 nm, were found on fibrinogen imprinted surface 12 following elution.

Figure 11:
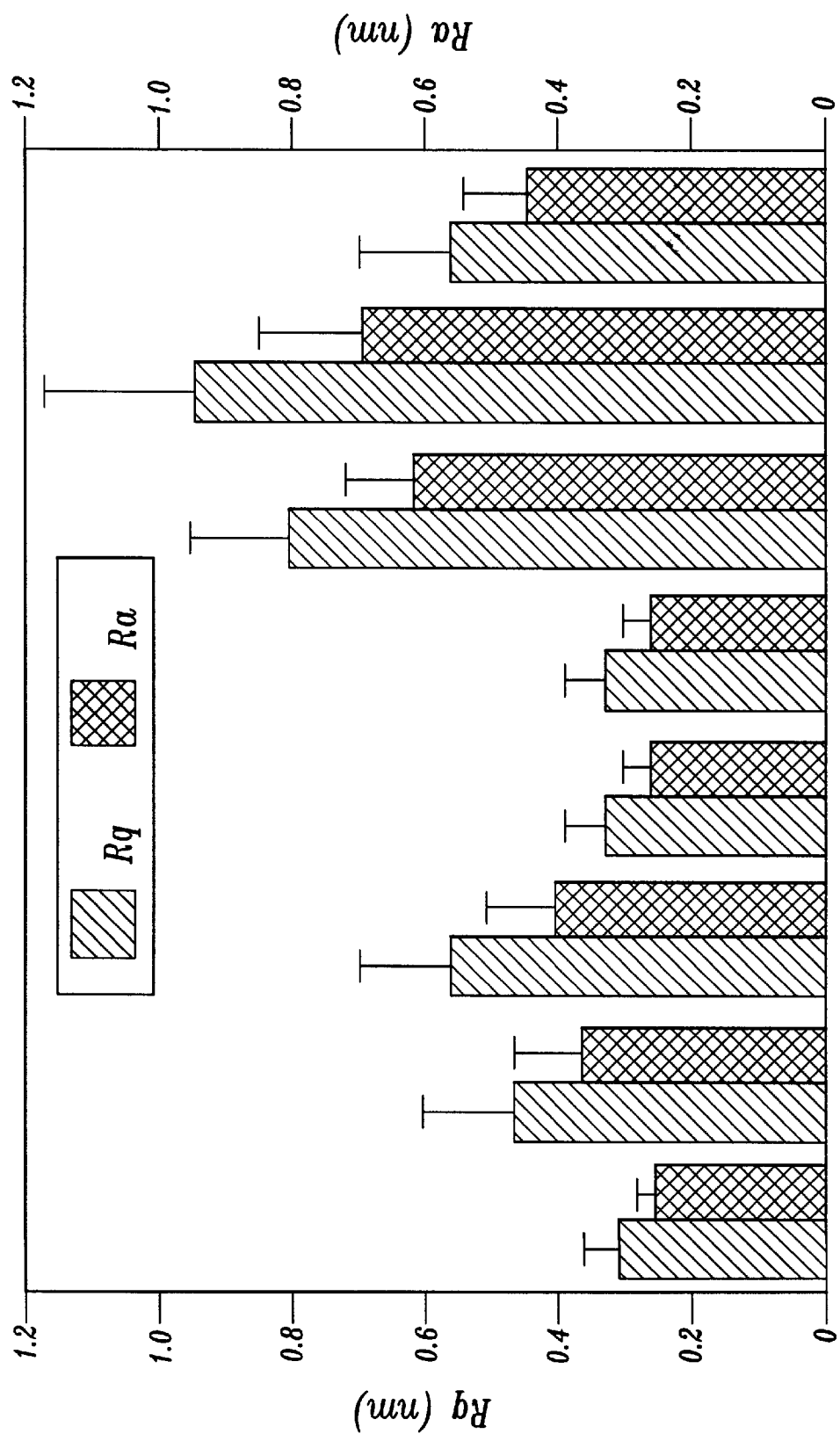
FIG. 11 shows averaged RMS roughness (Rq) and mean roughness (Ra) for protein-imprinted surfaces.

Statistical analysis of AFM data were also applied to the protein imprinted surfaces 12. Triplicate imprinted surfaces 12 were prepared for each kind of protein, IgG, albumin, and fibrinogen. Two images of 600×600 nm² were acquired at different spots of each sample. FIG. 11 shows the averaged RMS roughness ($R_q$) and mean roughness ($R_a$) for the protein-imprinted surfaces 12 and the control. Surface roughness values do not vary significantly for the non-protein control surfaces prior to, or following the NaClO/NaOH elution. Nonetheless, all the protein imprinted surfaces 12 following the elution are observed to have a considerable increase of surface roughness compared to those prior to the elution.

Figure 12:
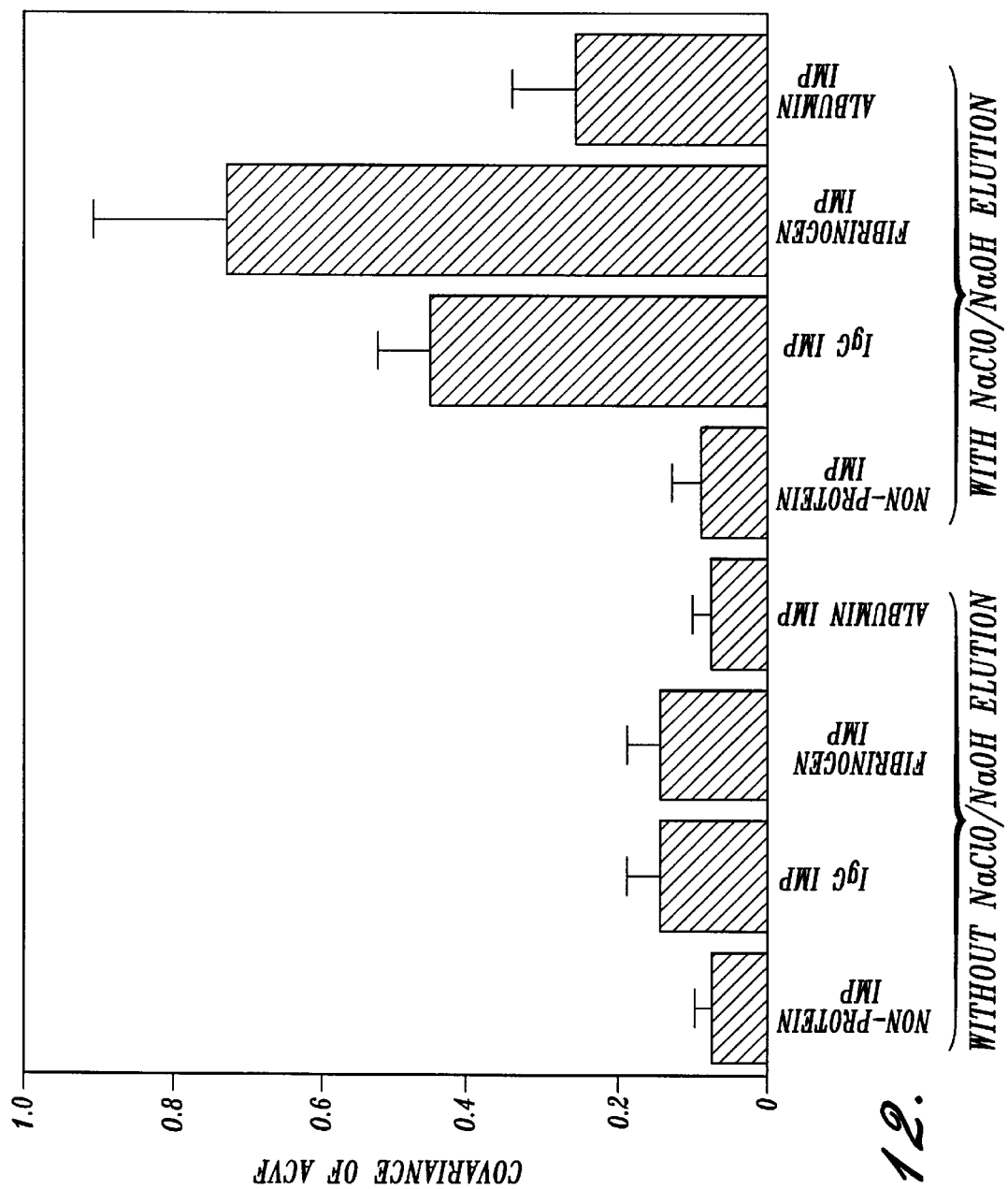
FIG. 12 shows averaged covariance values of the autocovariance function calculated for protein-imprinted surfaces and a control surface (n=6).

Since $R_q$ and $R_a$ are basically a measure of the variation in height, the limitation of these values as surface structural parameters is the lack of spatial information, e.g., roughness for surfaces with different spatial variation of features may be identical. Autocovariance, a measure of spatial correlation of heights, was used to complement roughness values in our surface topographic analysis. Covariance values of the autocovariance function calculated for the protein-imprinted surfaces 12 and the control are shown in FIG. 12. Following the elution, the control surface has a slightly larger covariance than that prior to the elution. However, the magnitude of increase after elution is much less than any one of the protein-imprinted surfaces 12, among which the fibrinogen imprinted surface has the largest covariance, followed by the IgG imprinted surface, and then the albumin imprinted surface. This is in agreement with the order of sizes, or molecular weights, of these imprinted proteins.

EXAMPLE 8

Chemistry of Imprinted Surfaces

Figure 13:
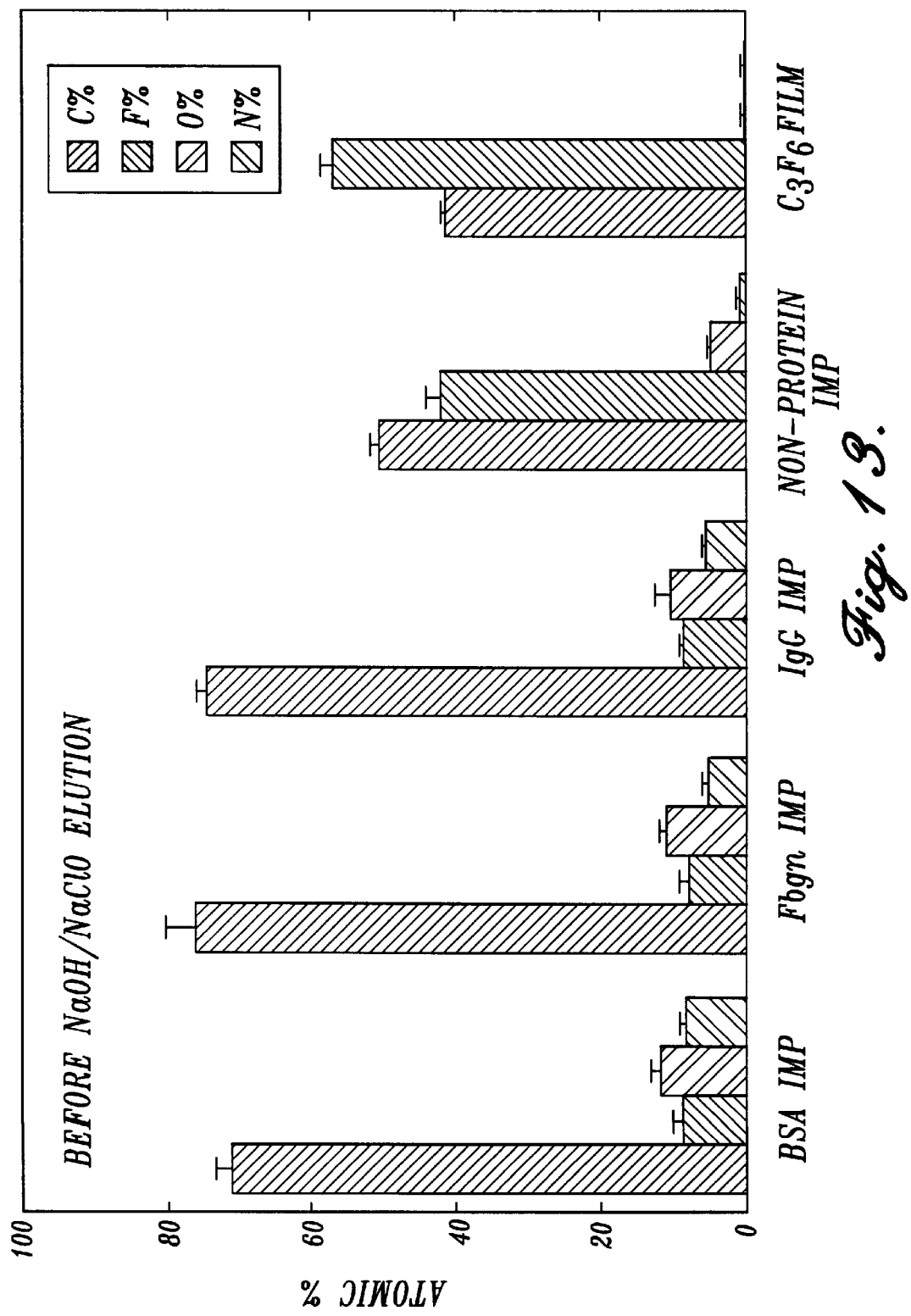
FIG. 13 shows the surface elemental composition of template-imprinted surfaces imprinted with albumin (BSA), fibrinogen (Fbgn) and IgG, a non-protein control imprint, and a $C_3F_6$ plasma deposited film, prior to NaOH/NaClO elution, as determined by ESCA.
Figure 14:
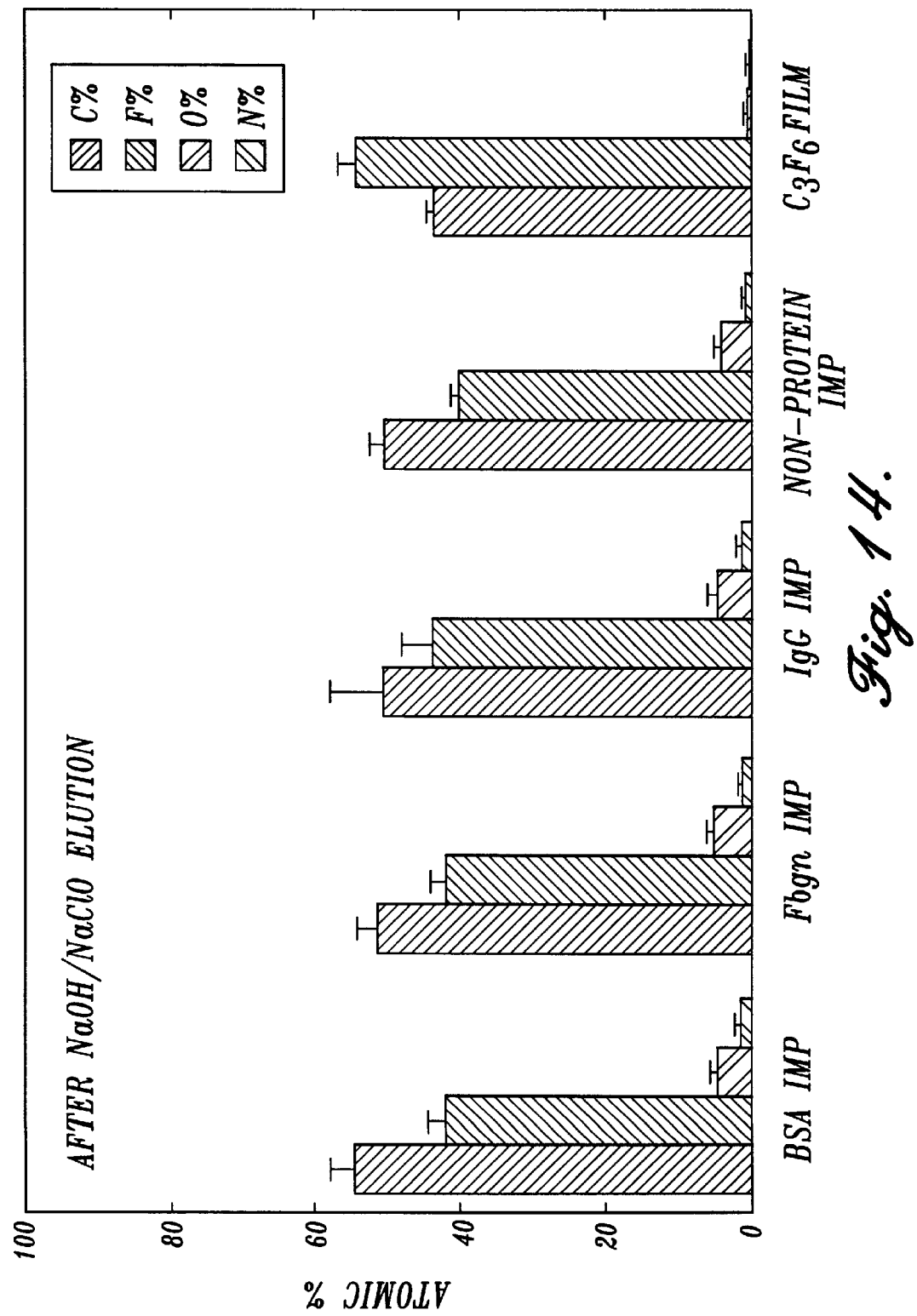
FIG. 14 shows the surface elemental composition of template-imprinted surfaces imprinted with albumin (BSA), fibrinogen (Fbgn) and IgG, a non-protein control imprint, and a $C_3F_6$ plasma deposited film following NaOH/NaClO elution, as determined by ESCA.

ESCA was used to determine the chemical composition of the top 100 Å of the surface of three protein imprinted surfaces 12 and two control surfaces; one control was the surface imprint of mica with only spin-cast trehalose, and the other was the imprint of plasma-deposited $C_3F_6$ (FIGS. 13 and 14, respectively). The NaClO/NaOH elution did not cause a big change in the elemental concentrations for the controls. However, the three protein imprinted surfaces 12 exhibited a similar change in surface chemistry following the elution: the nitrogen (N) content decreased drastically; carbon (C) and oxygen (O) showed a moderate drop, while the iron (F) content increased. The amount of N is a specific marker for the presence of proteins, since that is the only source of N in our system. Before the basic elution, N accounted for 10–11% of the total elemental concentration on the protein imprint surfaces, but after the basic elution N accounted for only 1–1.5%, which is close to the background N level of the control samples. These results show that most, if not all, protein was removed from the surface of protein imprinted surfaces 12 by elution. A high degree of similarity is also observed between the surface chemistry for the imprints of various proteins following elution, which further indicates the removal of different proteins from each imprinted surface 12.

Figure 15:
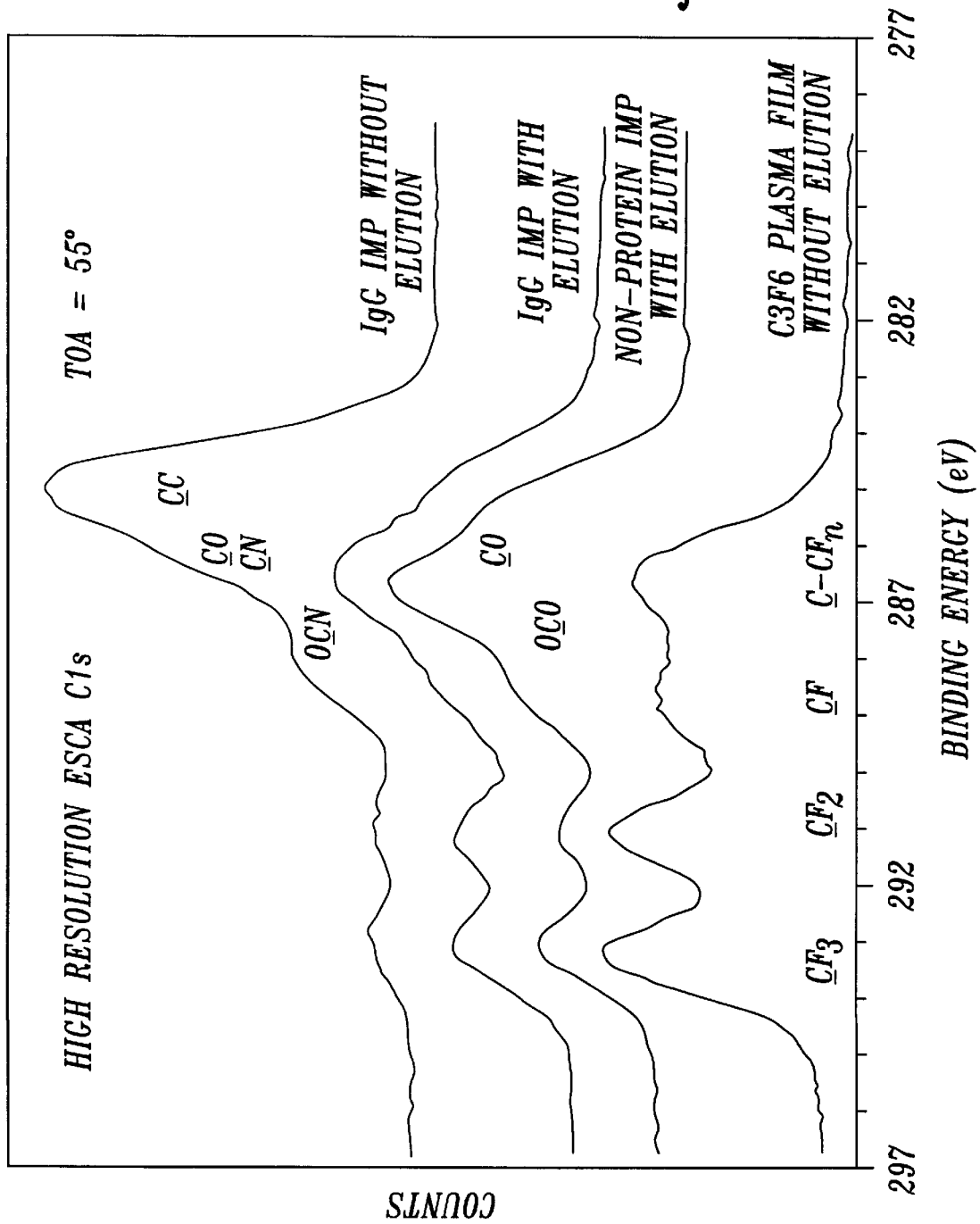
FIG. 15 shows high resolution ESCA C1s spectra of: an IgG template-imprinted surface prior to elution; an IgG template-imprinted surface following elution; a non-protein template-imprinted surface following elution, and a $C_3F_6$ plasma-deposited film prior to elution.
Figure 16:
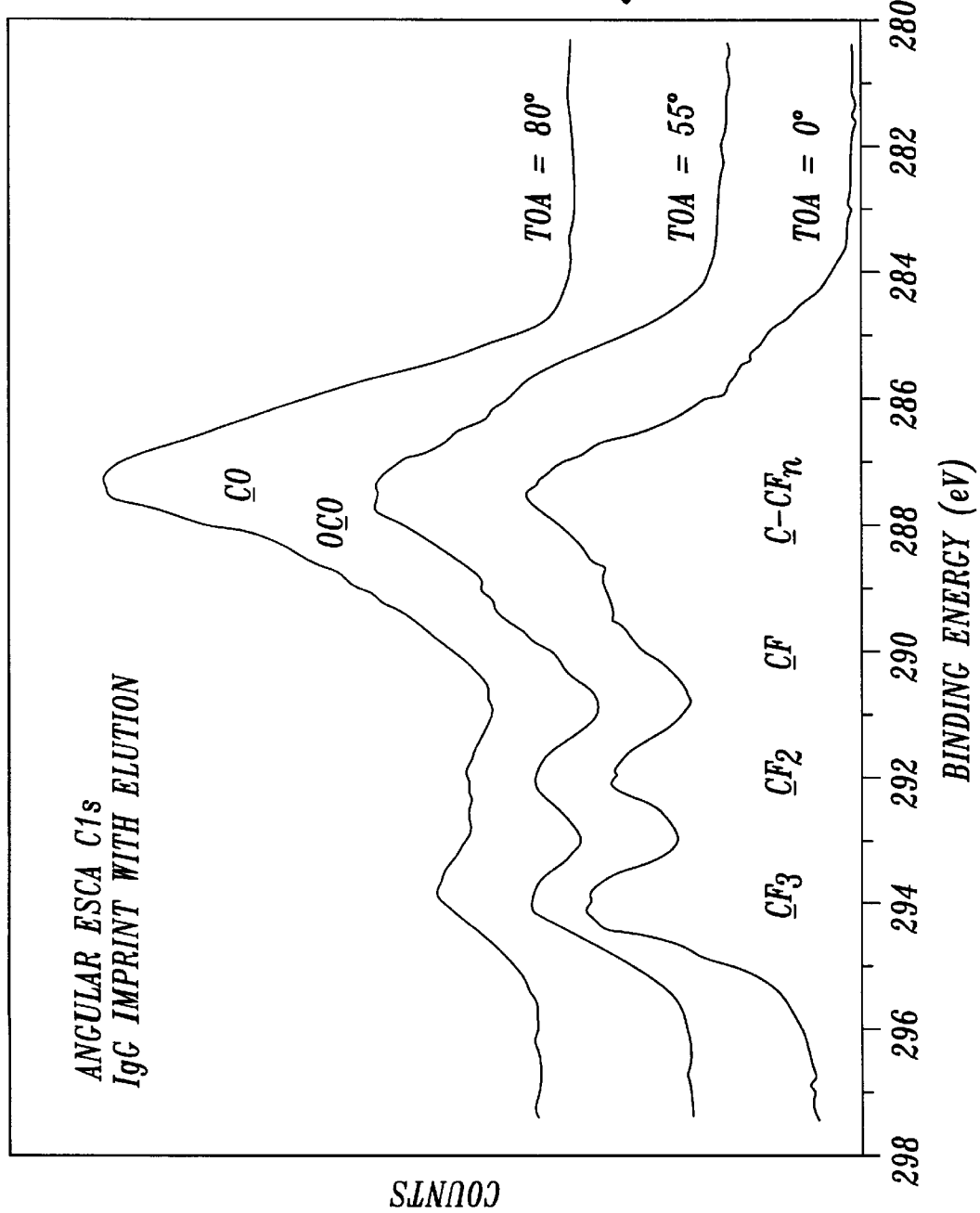
FIG. 16 shows ESCA C1s spectra of an IgG template-imprinted surface following elution at take-off angles of 0, 55 and 80.

FIG. 15 shows the ESCA C1s spectra for various imprinted surfaces 12. Compared to plasma deposited $C_3F_6$ film, the IgG imprinted surface 12 has quite a few big new peaks appearing near the hydrocarbon end, which could be assigned as C—C, CO, CN, and OCN, all of which are possibly the contributions of protein. The much smaller peaks of $CF_3$ and $CF_2$ in the IgG imprinted surface 12 prior to elution suggests the masking of the underlying plasma fluoropolymer by the protein overlayer. Following the elution, the spectra of the IgG imprinted surface 12 becomes very much like that of the control imprint of sugar. The hydrocarbon peak is much reduced, while the $CF_3$ and $CF_2$ peaks is lifted. These data indicate the removal of some surface proteins. The CO and OCO peaks associated with sugar could be assigned in the big envelope. The surface enrichment of sugar with the protein imprint is best demonstrated by the angular studies of C1s spectra (FIG. 16). As the take-off angles increases, more and more top surface is exposed to X-ray. It is obvious that sugar content is the highest at the topmost portion of protein-imprinted surface 12, as evidenced by the change of peak intensities for CO and OCO.

EXAMPLE 9

Analysis of Imprinted Surfaces Using ToF SIMS

Figure 17:
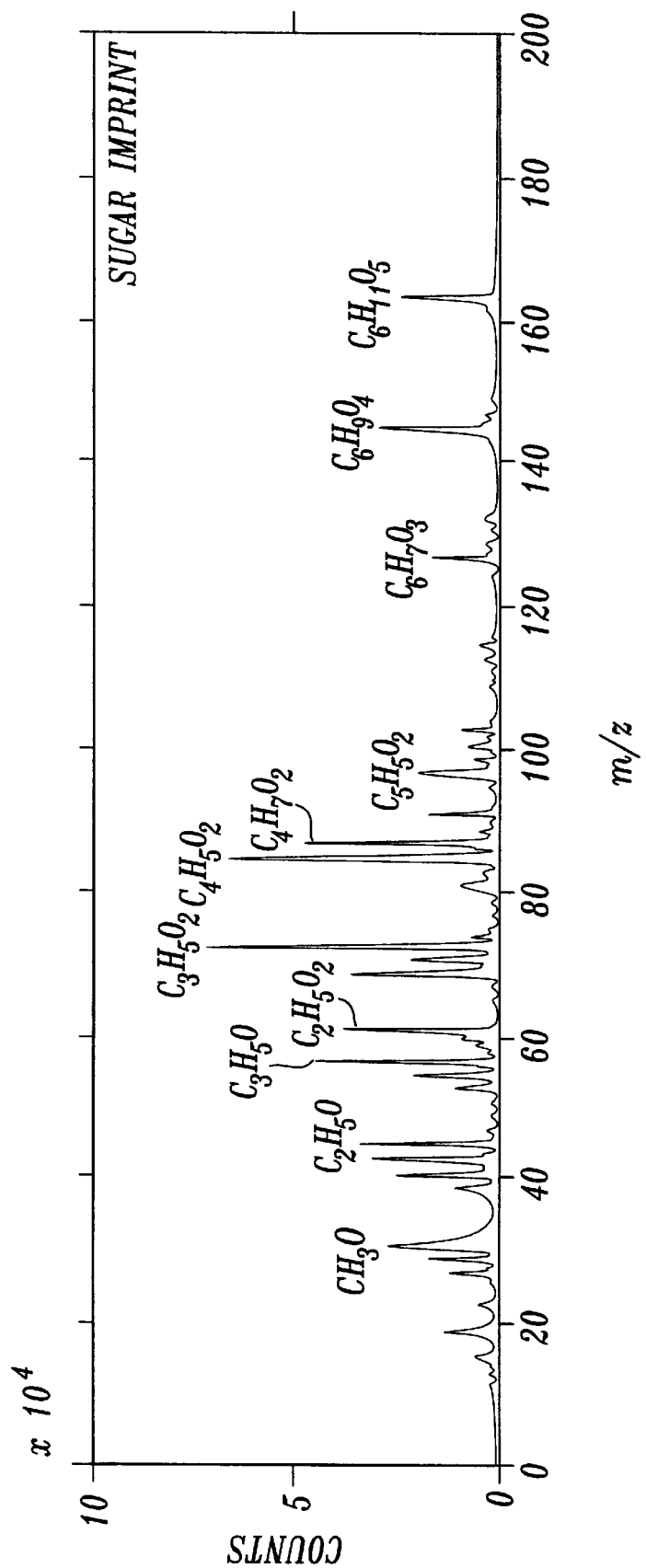
FIG. 17 shows a positive-ion ToF-SIMS spectrum (0–200 m/z) of a template imprinted surface imprinted only with trehalose.
Figure 18:
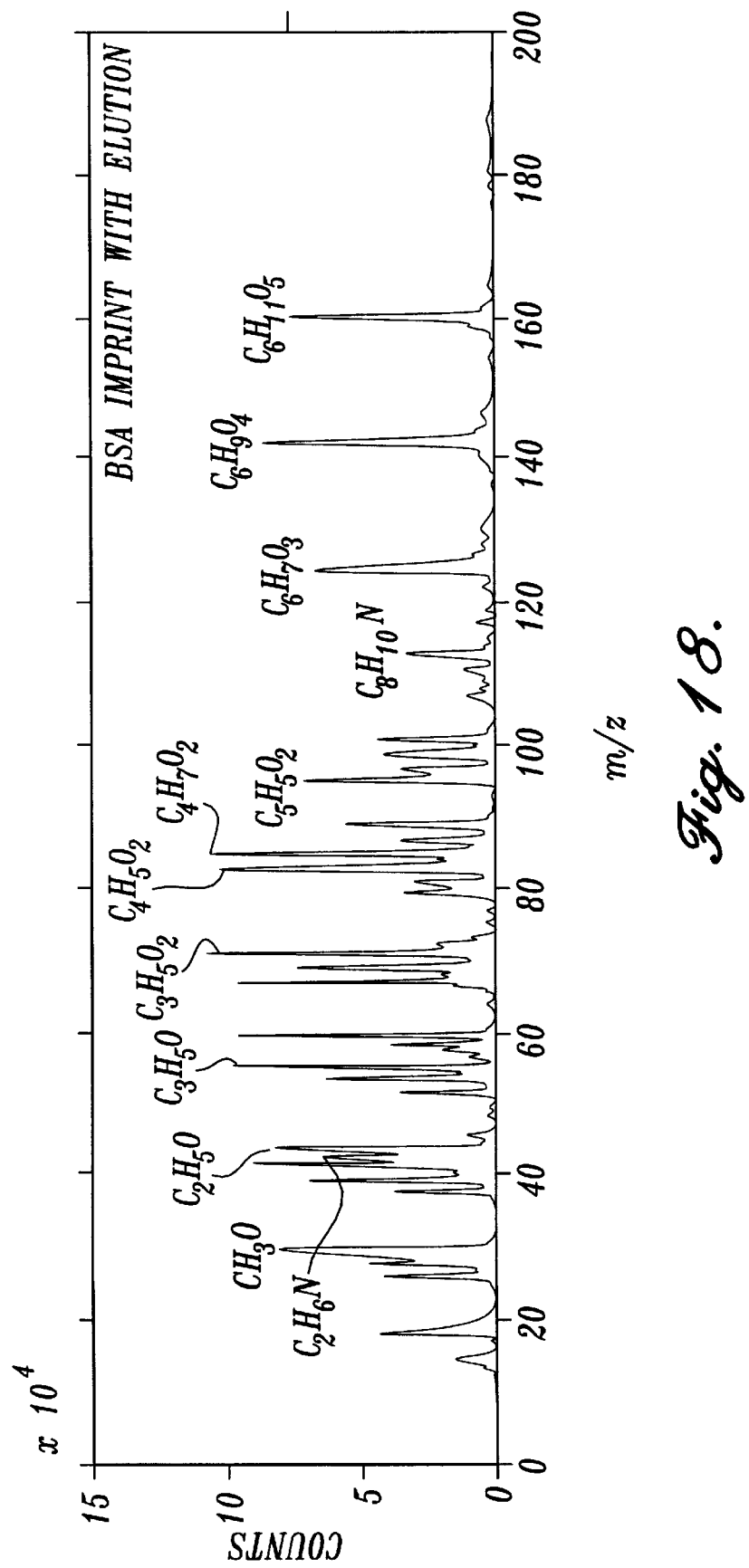
FIG. 18 shows a positive-ion ToF-SIMS spectrum (0–200 m/z) of a template imprinted surface, imprinted with BSA, following NaOH/NaClO elution.
Figure 19:
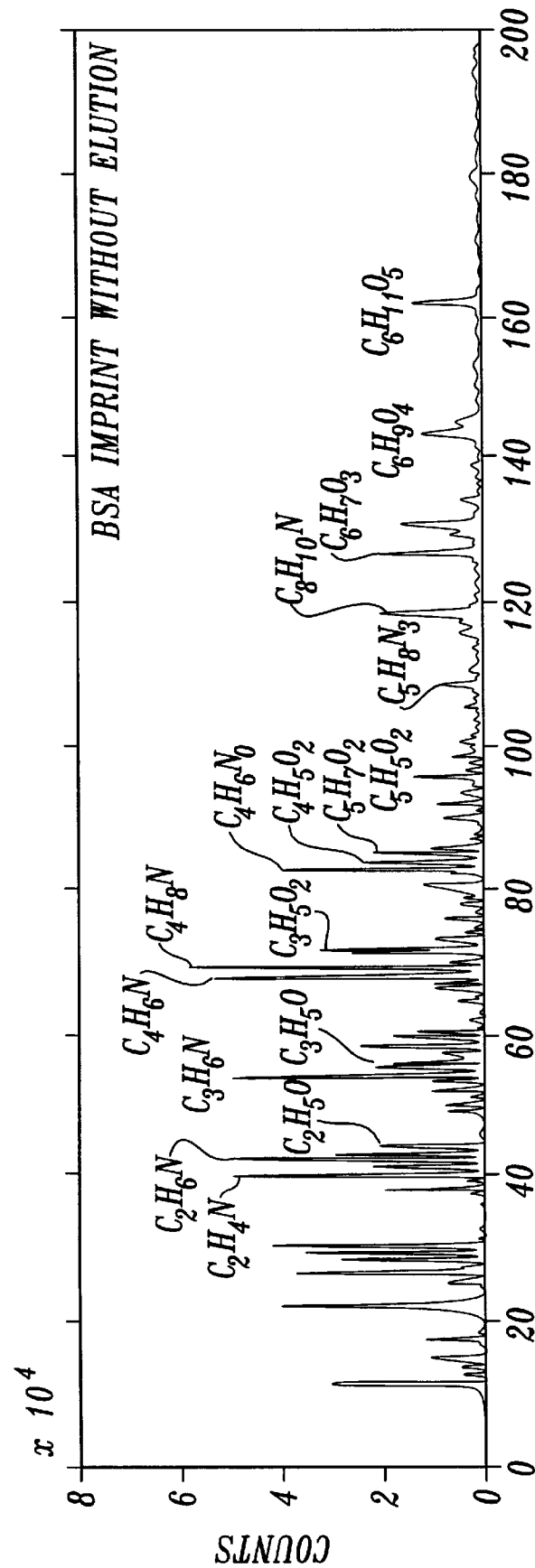
FIG. 19 shows a positive-ion ToF-SIMS spectrum (0–200 m/z) of a template imprinted surface, imprinted with BSA, prior to NaOH/NaClO elution.

The top 10–15 Å of protein-imprinted surfaces 12 were interrogated by ToF-SIMS. The typical positive secondary ion mass spectra (m/z 0–200) of the imprinted surfaces 12 are shown in FIGS. 17, 18 and 19. The surface of the BSA imprinted surface 12 (FIG. 19) prior to elution is found to have both a protein moiety, whose major peaks are m/z 42 $C_2H_4N^+$, 44 $C_2H_6N^+$, 56 $C_3H_6N^+$, 68 $C_4H_6N^+$, 70 $C_4H_8N^+$, 84 $C_4H_6NO^+$, 110 $C_5H_8N_3^+$ and 120 $C_8H_{10}N^+$, as well as sugar species (m/z 45 $C_2H_5O^+$, 57 $C_3H_5O^+$, 73 $C_3H_5O_2^+$, 85 $C_4H_5O_2^+$, 87 $C_4H_7O_2^+$, 97 $C_5H_5O_2^+$, 127 $C_6H_7O_3^+$, 145 $C_6H_9O_4^+$ and 163 $C_6H_{11}O_5^+$). However, the relative peak intensities of the protein associated peaks are much higher than those of the sugar peaks. These data suggest that more protein moiety is on the just reversed replica surface prior to elution. As shown in FIG. 18, however, following the basic elution the situation reverses. Sugar associated peaks of much higher intensities appear on the BSA imprinted surface 12, while the protein peaks decrease to a very insignificant portion. Actually, the spectrum of the BSA imprinted surface 12 looks surprisingly like that of the control imprint of sugar, except for some small peaks from the protein, of which several, such as m/z 44 $C_2H_6N^+$, 70 $C_4H_8N^+$ and 120 $C_8H_{10}N^+$, were chosen and labeled for illustration. Interestingly, the fluorine ions from plasma deposited film 16 do not contribute much to all these surfaces. $CF^+$ 31 is present in each sample, but in general is present in very low amounts (less than 2% of the total counts).

Figure 20:
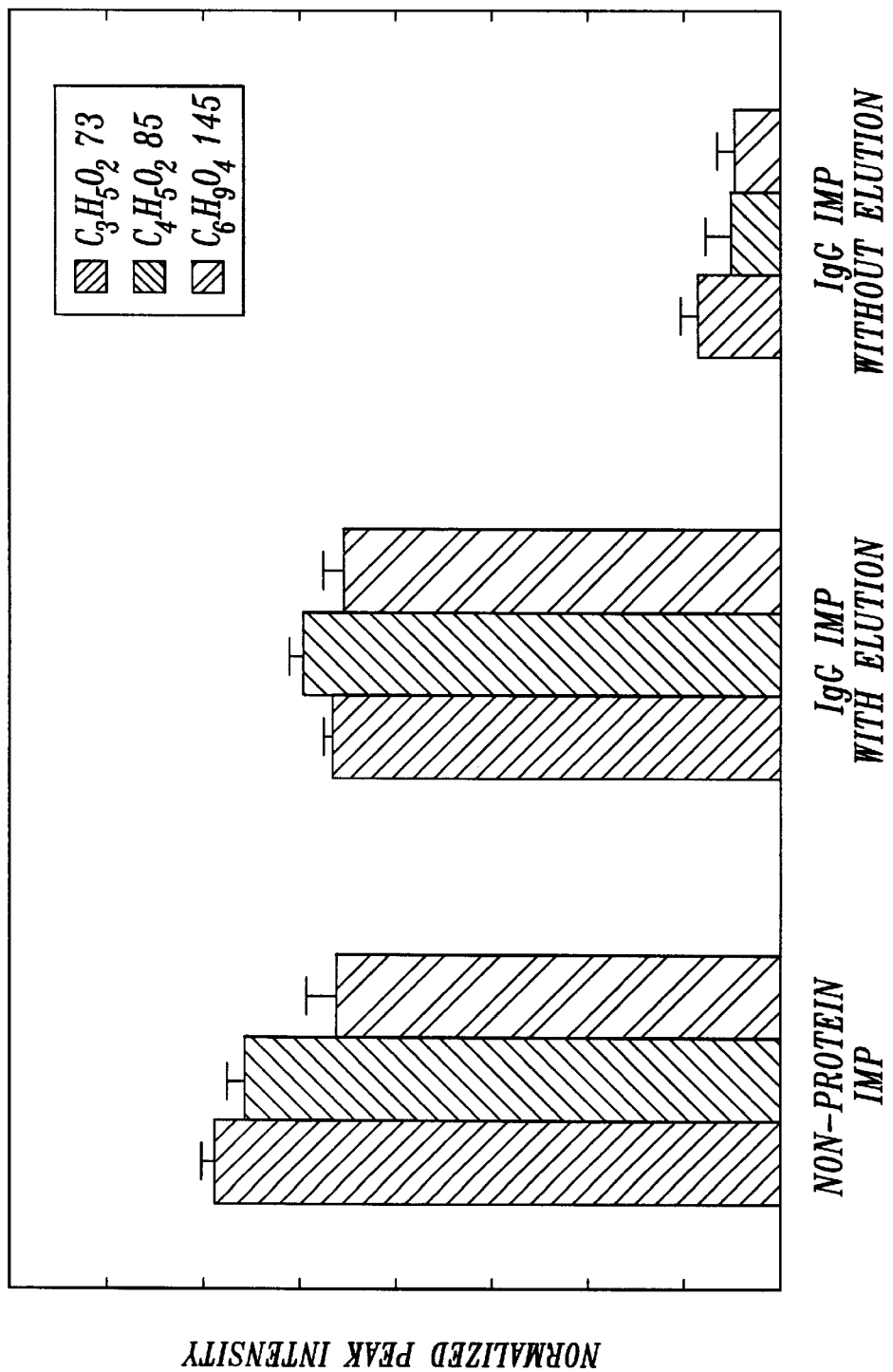
FIG. 20 shows the intensities of selected ToF-SINS peaks from template-imprinted surfaces imprinted only with trehalose. All the peaks were normalized on total counts.
Figure 21:
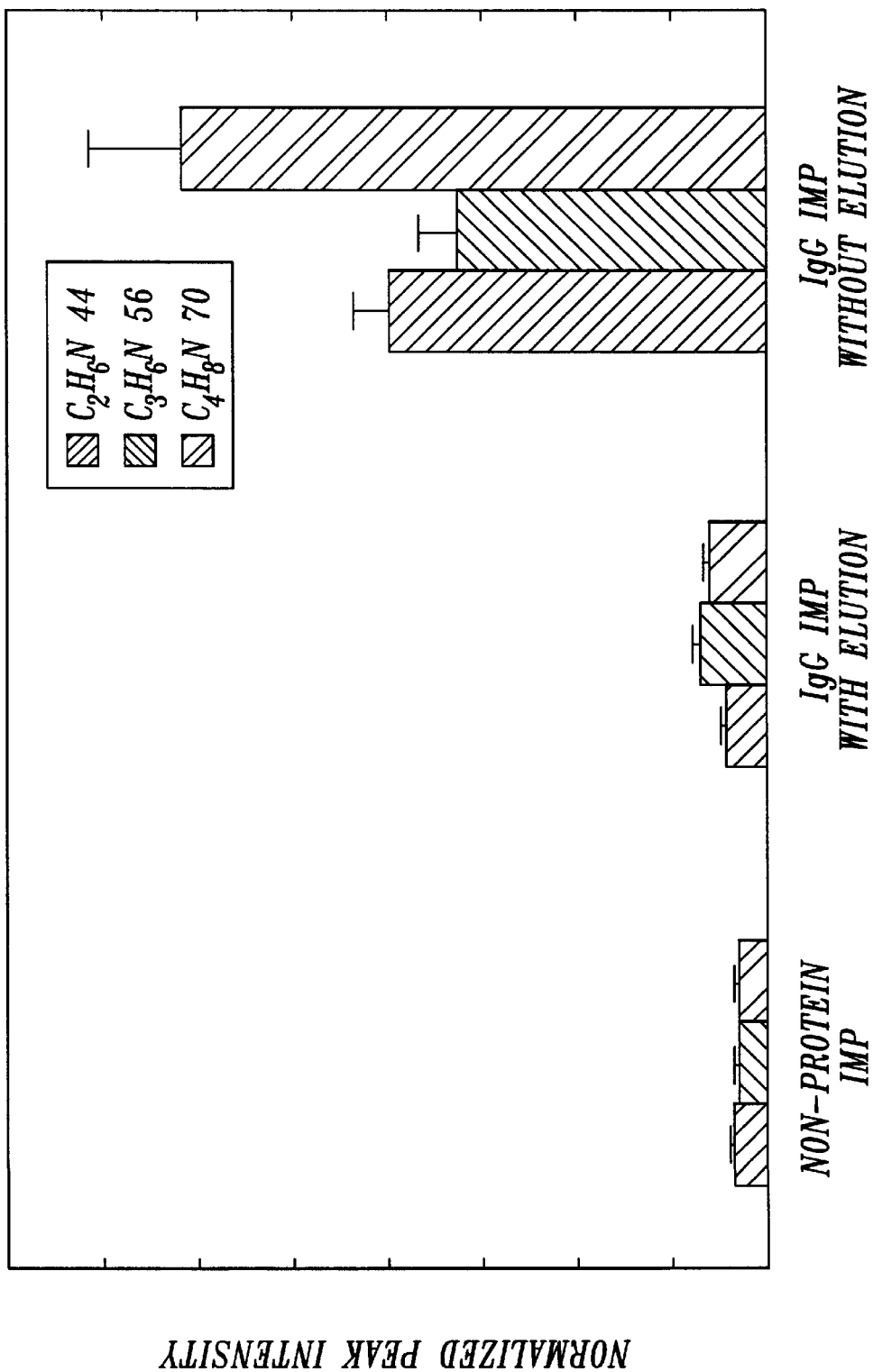
FIG. 21 shows the intensities of selected ToF-SINS peaks from template-imprinted surfaces imprinted with protein. All the peaks were normalized on total counts.

To quantitatively investigate the effectiveness of the basic elution, several characteristic peaks of sugar (73 $C_3H_5O_2^+$, 85 $C_4H_5O_2^+$ and 145 $C_6H_9O_4^+$) and proteins (44 $C_2H_6N^+$, 56 $C_3H_6N^+$ and 70 $C_4H_8N^+$) were chosen to monitor the change of their peak intensities before and after the elution (FIGS. 20 and 21). All the peaks were normalized on the total counts. As expected, the intensities of protein associated peaks are almost of an order higher on the protein (IgG) imprinted surface 12 prior to the elution than on the non-protein imprint which only imprint sugar, and the protein imprint following the elution. On the contrary, the sugar associated peaks on the latter two imprinted surfaces 12 are much higher in intensity than the former, the protein imprint without elution.

Principal component analysis (PCA), a multivariate data exploration method, were applied to multiple sets of our ToF-SIMS spectra of the imprints to assess the reproducibility of our sample preparation. The first principal component captures 87% of the variance and the second captures another 7%. The combination of these first two principal components gives a satisfactory description of the imprint surfaces 12. The plot of the first principal component vs. the second separates well the three different kinds of surfaces: protein imprinted surface 12 prior to elution, protein imprinted surface 12 following elution, and the sugar imprint control (data not shown). These data demonstrated a statistical surface homogeneity with the protein imprinted surfaces 12 that were prepared.

EXAMPLE 10

Contact Angle Analysis of Template-Imprinted Surfaces

The advancing contact angles of template-imprinted surfaces 12 before and after elution of templates 24 were measured (Table II).

TABLE II

Static Advancing Contact Angles of Water in Air (n = 3)

| | Before NaOH/NaClO elution (degrees ± s.d.) | After NaOH/NaClO elution (degrees ± s.d.) |
|---|---|---|
| $C_3F_6$ plasma film | 112 ± 2 | 105 ± 5 |
| Albumin (BSA) imprint | 22 ± 13 | 30 ± 7 |
| IgG imprint | 31 ± 15 | 33 ± 9 |
| Fibrinogen (Fbgn) imprint | 19 ± 17 | 25 ± 11 |
| Non-protein imprint | 38 ± 4 | 35 ± 7 |

Compared to the plasma deposited fluoropolymers, all the imprinted surfaces 12, before or after basic treatment, are very hydrophilic. In the case of protein imprinted surfaces 12 before elution, the contact angles are slightly lower than their counterparts after elution, but their standard deviation is also larger, which is presumably due to the effect of the uneluted surface protein. The difference of contact angle values between the control sugar imprint with or without elution is negligible. These data suggest that the elution exerts an insignificant effect on the sugar layer. Following the elution, each protein imprinted surface 12, as well as the control sugar imprint, has a contact angle value centered around 25 and 30 degrees, which indicates the hydrophilic nature of our imprint surfaces, compared to most polymers.

EXAMPLE 11

Amount of Protein Adsorbed by Imprinted Surface from Single Protein Solutions

The adsorption of protein from a single solution was performed to determine the amount of protein binding to template-imprinted surfaces 12 and to qualitatively evaluate the interactions between template protein 24 and template-imprint surfaces 12.

Figure 22:
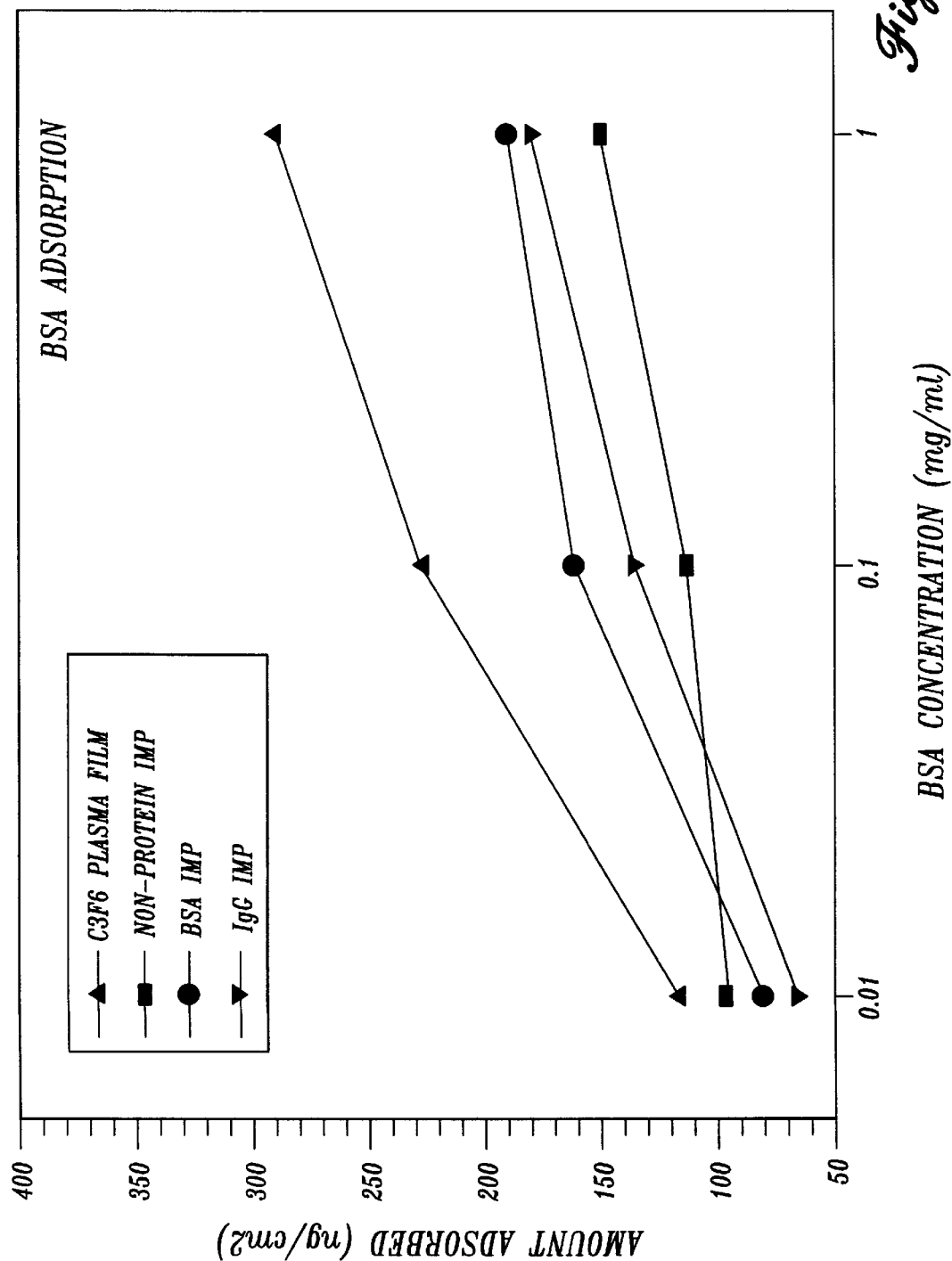
FIG. 22 shows the adsorption of albumin on various template-imprinted surfaces from different concentrations of protein solution.
Figure 23:
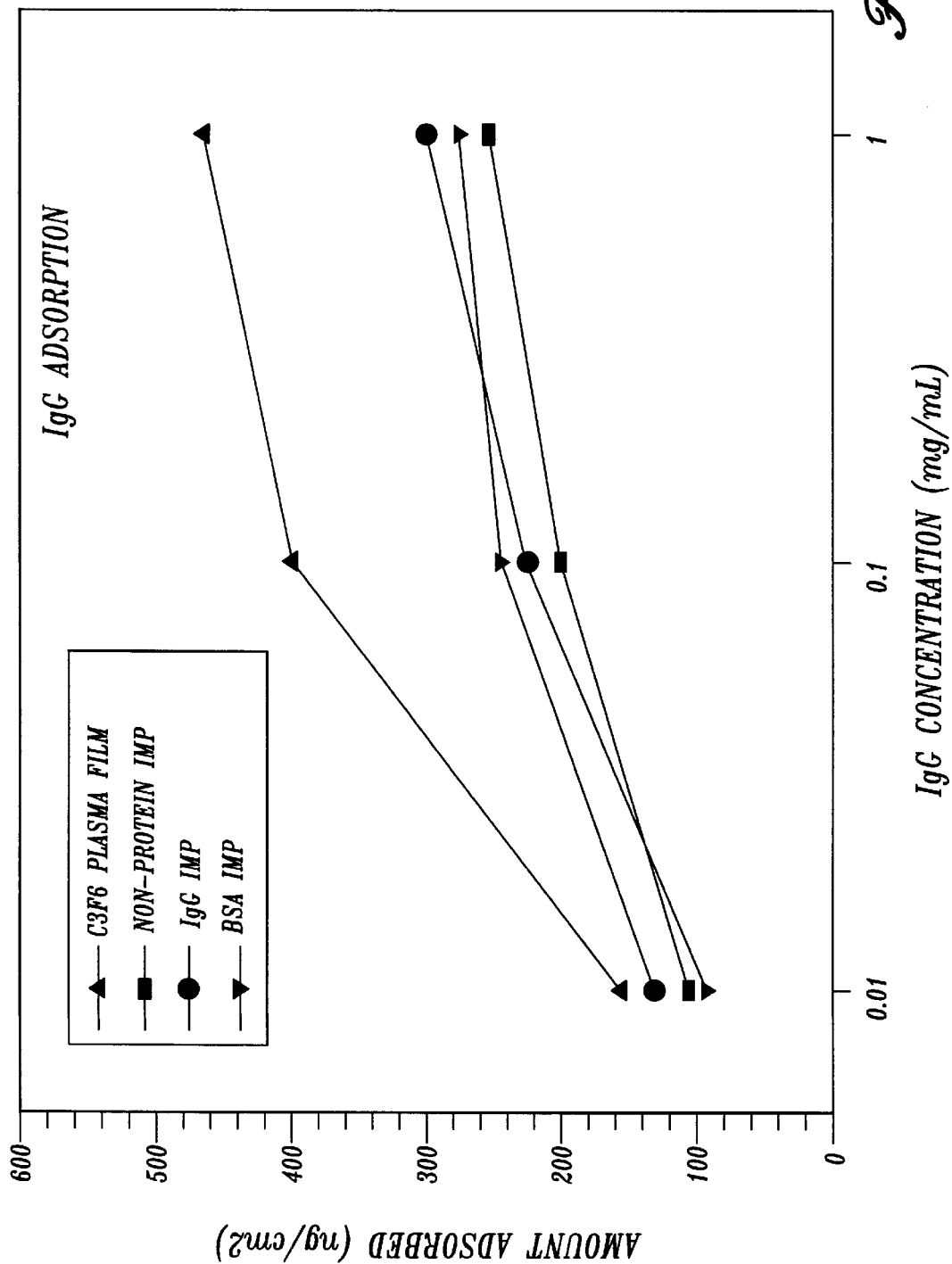
FIG. 23 shows the adsorption of IgG on various template-imprinted surfaces from different concentrations of protein solution.
Figure 24:
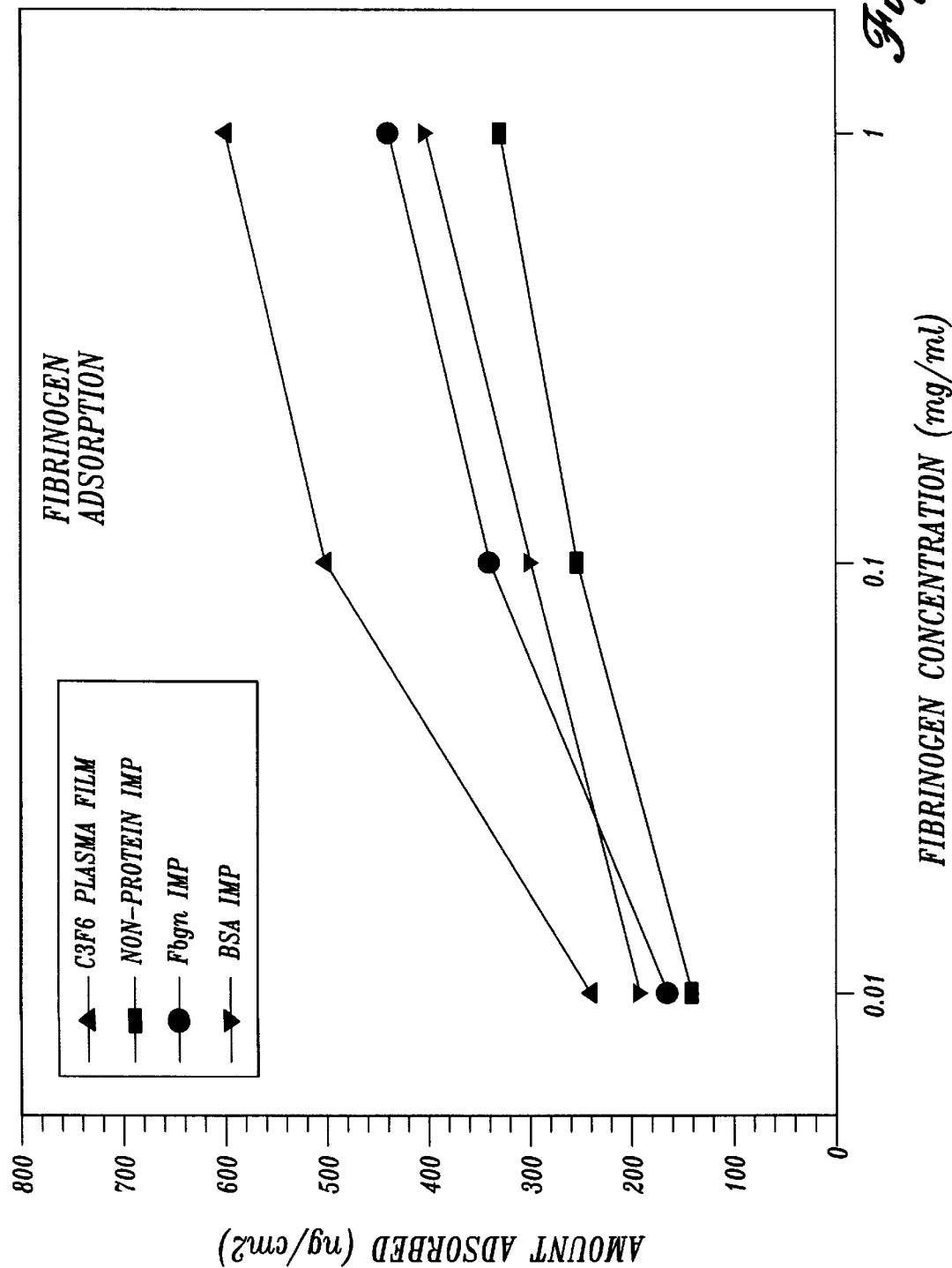
FIG. 24 shows the adsorption of fibrinogen on various template-imprinted surfaces from different concentrations of protein solution.

Adsorption of $^{125}$I-labeled albumin (FIG. 22), IgG (FIG. 23) and fibrinogen (FIG. 24) by template-imprinted surfaces 12 from solutions of different concentrations (0.01, 0.1 and 1 mg/mL) was performed on various protein imprinted surfaces 12 and controls. Plasma deposited fluoropolymer was used as a positive control, since it is known to bind proteins tenaciously and in large amounts. As the concentration of protein solution increased, more protein was adsorbed to each surface 12. The amount of protein adsorbed was slightly higher on the protein-imprint surfaces 12 than on a non-protein imprinted surface, which suggests a larger surface area induced by imprinting. However, no significant difference was found between the amount of protein adsorbed on different protein imprinted surfaces 12. This non-discrimination could be explained by the existence of non-specific protein adsorption that mask the specific binding.

EXAMPLE 12

Surfactant Elution of Protein Adsorbed from Single Solutions

To evaluate the protein binding strength, the removal or elution of adsorbed proteins from template-imprinted surfaces 12 was accomplished using a solution of surfactant, polyoxyethylenesorbitan monolaurate (Tween-20) or sodium dodecyl sulfate (SDS). The resistance to detergent solubilization has been reported to be indicative of the protein binding strength. Differences in the elutability of an adsorbed protein reflect changes in the protein structure or the protein-surface interaction strength. The retention of adsorbed protein following Tween-20 or SDS exposure was thus measured to determine the effect of template imprinting on protein-imprint binding strength.

Figure 25:
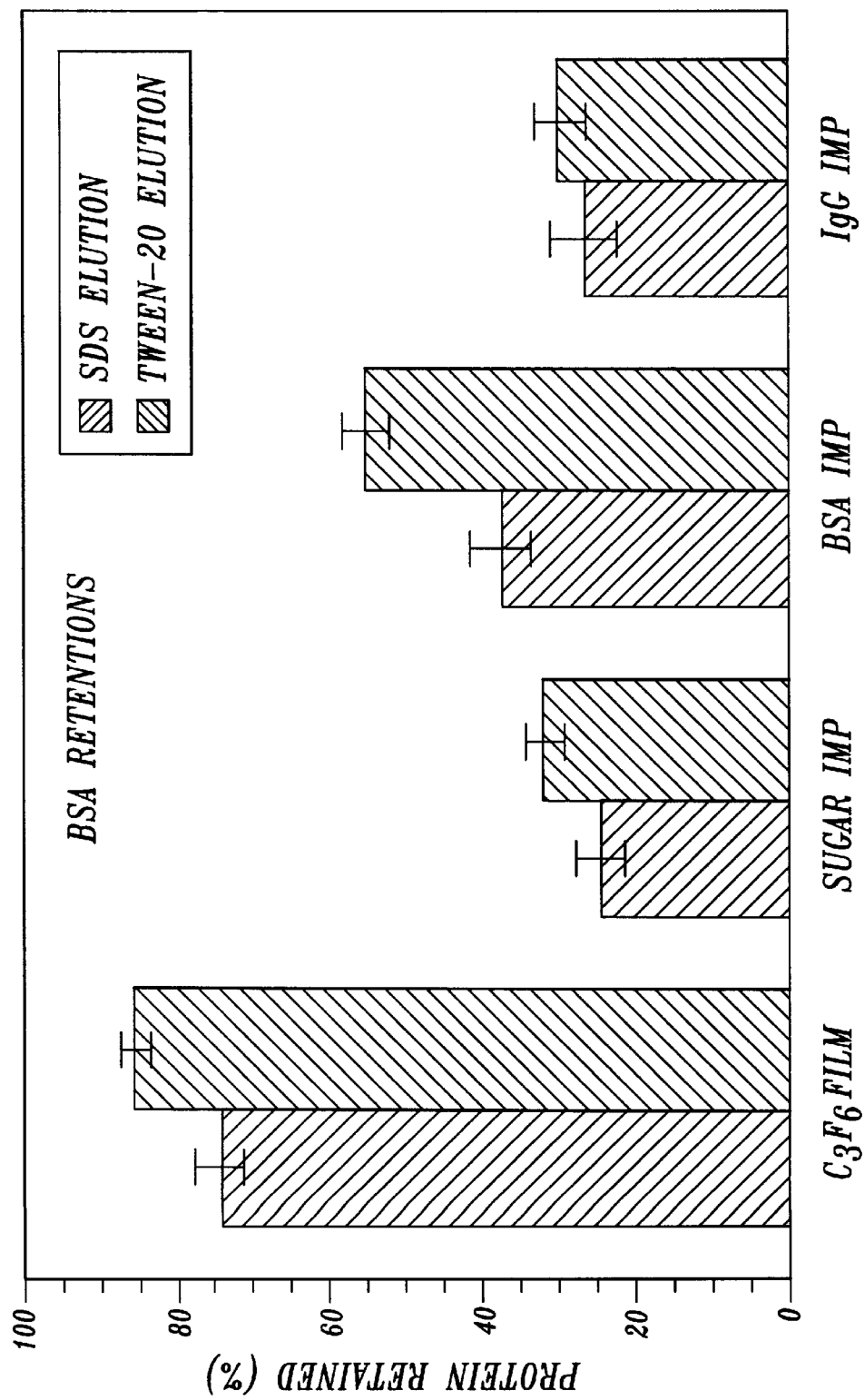
FIG. 25 shows the retention of albumin on various template-imprinted surfaces following elution with SDS or Tween-20. The resistance to detergent elution is indicative of the protein binding affinity. The albumin was adsorbed from a 0.1 mg/ml solution.
Figure 26:
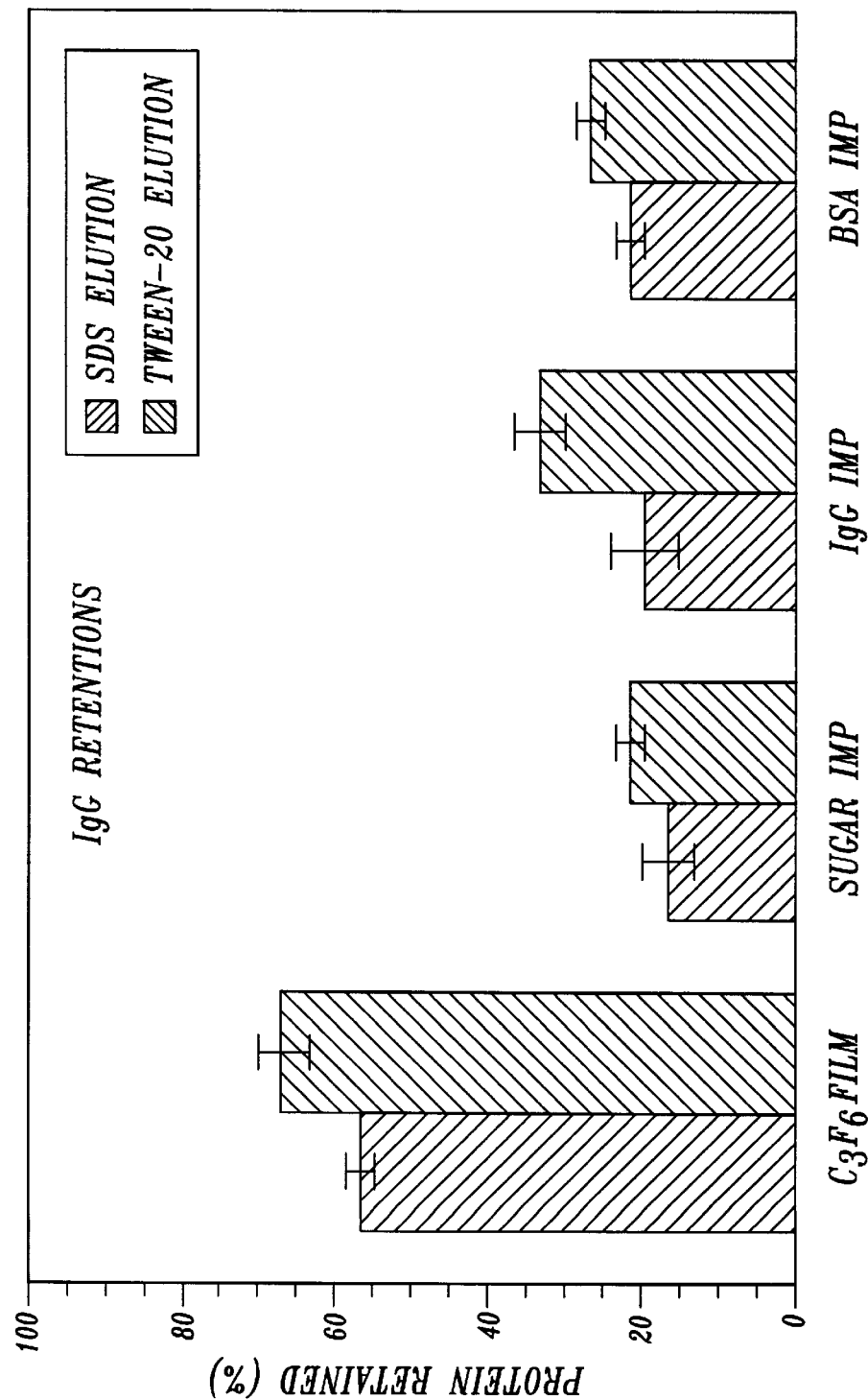
FIG. 26 shows the retention of IgG on various template-imprinted surfaces following elution with SDS or Tween-20. The resistance to detergent elution is indicative of the protein binding affinity. The IgG was adsorbed from a 0.1 mg/ml solution.
Figure 27:
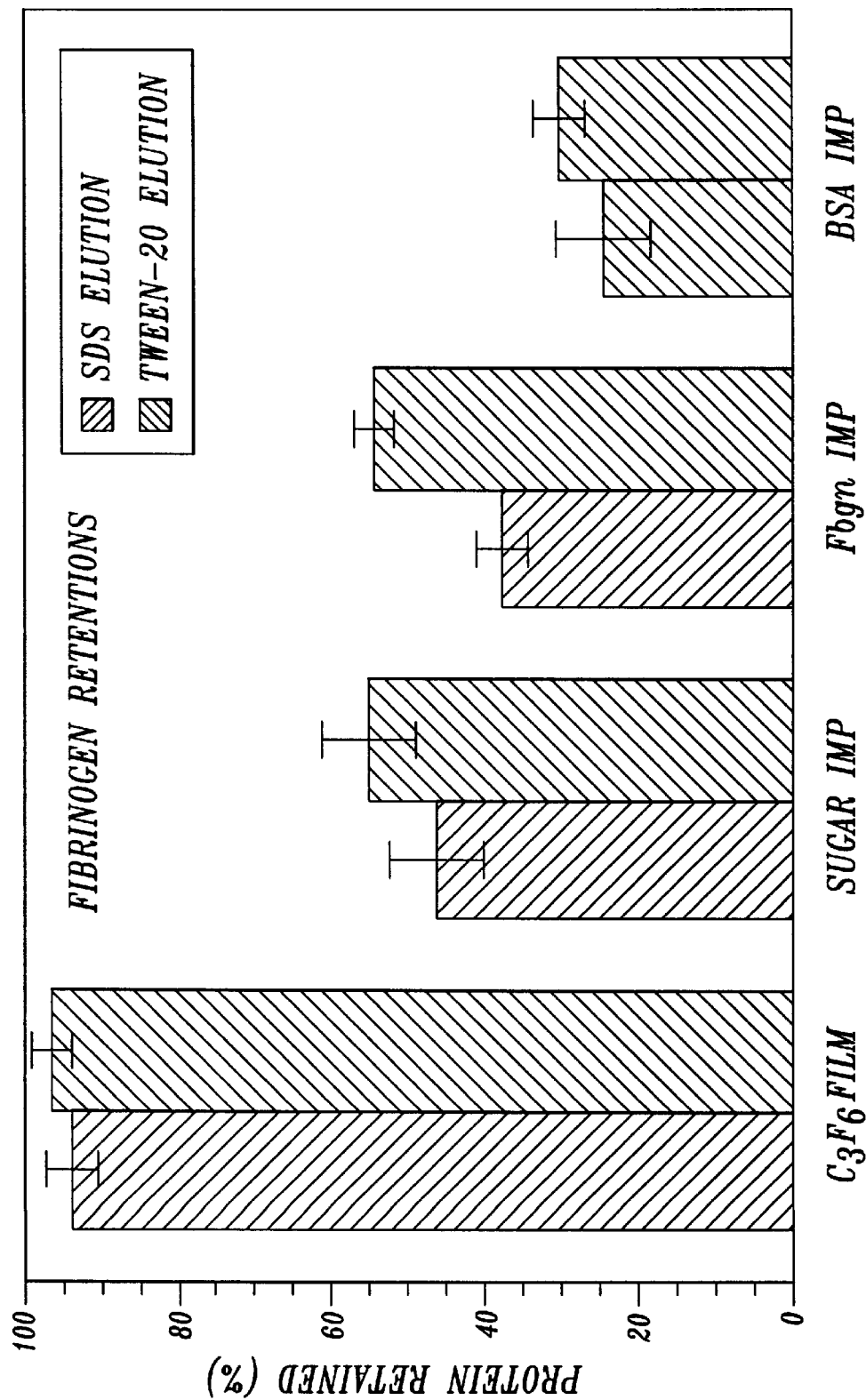
FIG. 27 shows the retention of fibrinogen on various template-imprinted surfaces following elution with SDS or Tween-20. The resistance to detergent elution is indicative of the protein binding affinity. The fibrinogen was adsorbed from a 0.1 mg/ml solution.

The amount of protein remaining on surface 12 following a detergent elution varies between surfaces 12. The imprinted surface 12 of a particular protein often retains more of its template protein 24 than the imprinted surface 12 of another protein or the sugar imprint control, when template protein 24 is albumin (FIG. 25) or IgG (FIG. 26), rather than fibrinogen (FIG. 27). This implies that template protein 24, as a population, binds to its imprinted surface 12 with a higher affinity than a non-template protein. It was noticed that the detergent elution did not remove all the proteins from imprint surfaces 12, e.g., with the control sugar imprint there is always 15–25% protein remaining following the detergent elution. Considering the heterogeneity of the adsorbed states of proteins, these non-elutable proteins are presumed to bind surfaces non-specifically yet with high strengths, while a larger fraction of proteins adsorb on hydrophilic surfaces non-specifically and weakly. The effect of preferential retention of template protein 24 is more obvious with the use of Tween-20 instead of SDS. It could be that the specific protein binding via hydrogen bonding is of modest affinity in nature, thus, a mild detergent such as Tween-20 is more appropriate to use to differentiate those weak, non-specific adsorption from the specific binding.

EXAMPLE 13

Competitive Adsorption of Protein From Binary Mixtures

A direct assessment of protein recognition by template-imprinted surfaces 12 was obtained by investigating competitive protein adsorption from a binary mixture, of which one protein is the template protein 24 used to imprint surface 12, and the other is a competing, non-template protein. Competitive adsorption of $^{125}$I labeled protein to surfaces 12 were performed from a series of solutions containing an additional unlabeled protein. The series of mixture solutions covered a wide range of competing to labeled protein ratios (typically $10^{-3}$ to $10^2$). The resulting curves were then analyzed to determine the competitive effectiveness and relative affinity of the competing proteins. In those experiments, the $^{125}$I protein concentration is held constant and only the competing protein concentration is varied. The ratio of competing protein to labeled protein required to cause $^{125}$I protein adsorption to drop to 50% of its noncompeting value is an estimate of the relative affinity of the unlabeled protein compared to the labeled protein.

Two binary protein mixture systems were investigated: IgG and albumin (BSA), and lysozyme (LSZ) and ribonuclease A (RNase). The former pair of proteins are among the most abundant plasma proteins, and have been commonly studied for their interactions with biomaterials. LSZ and RNase are relatively small proteins that have similar molecular weights and shapes. They also have many similar physiochemical properties, e.g., isoelectric point, overall and surface hydrophobicity and Gibbs energy of denaturation (Table III), which heavily influence their surface adsorption behavior.

TABLE III

Some Physico-Chemical Properties of the Proteins
Lysozyme (LSZ), Ribonuclease (RNase) and α-lactalbumin (α-LA)

|  | LSZ | RNase | α-LA |
|---|---|---|---|
| Molar mass (D) | 14,600 | 13,68 | 14,200 |
| Dimensions (nm$^3$) | 4.5 × 3.0 × 3.0 | 3.8 × 2.2 × 2.2 | 3.7 × 3.2 × 2.5 |
| Isoelectric point (pH units) | 11.1 | 9.4 | 4.3 |
| Overall hydrophobicity (J/g) | −7.6 | −8.7 | −5.8 |
| Apolar surface fraction | 41 | 46 | ? |
| Gibbs energy of denaturation (J/g) | | | |
| Heat | −4.1 | −3.2 | −1.5 |
| Denaturant 1 | −4.0 | −3.9 | −1.9 |
| Denaturant 2 | −2.6 | −2.2 | −1.3 |

Figure 28:
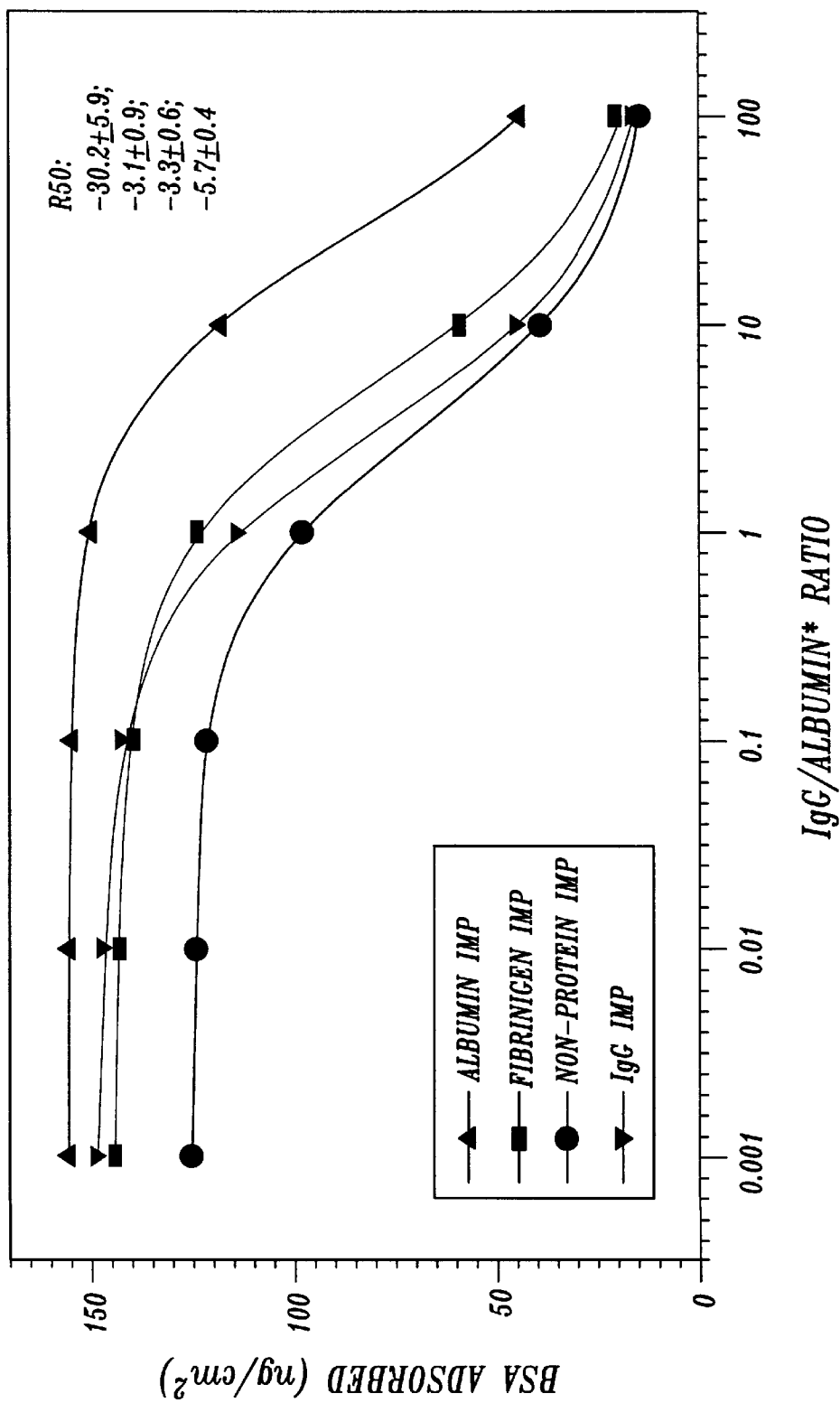
FIG. 28 shows competitive adsorption of $^{125}I$ labeled albumin (*) against unlabeled IgG on template-imprinted surfaces. Data are averages of triplicated samples. Error bars are omitted for clarity. Kaleidagraph™ was used to fit a curve to an equation. The ratio of unlabelled protein to labelled protein required to cause a 50% reduction in the maximum albumin adsorption (R50) was determined for each template-imprinted surface: albumin imprint (30.2±5.9); IgG imprint (3.1±0.9); fibrinogen imprint (5.7±0.4) and non-protein imprint (3.3±0.6). This R50 value is indicative of the binding affinity of the labelled protein to a template-imprinted surface.
Figure 29:
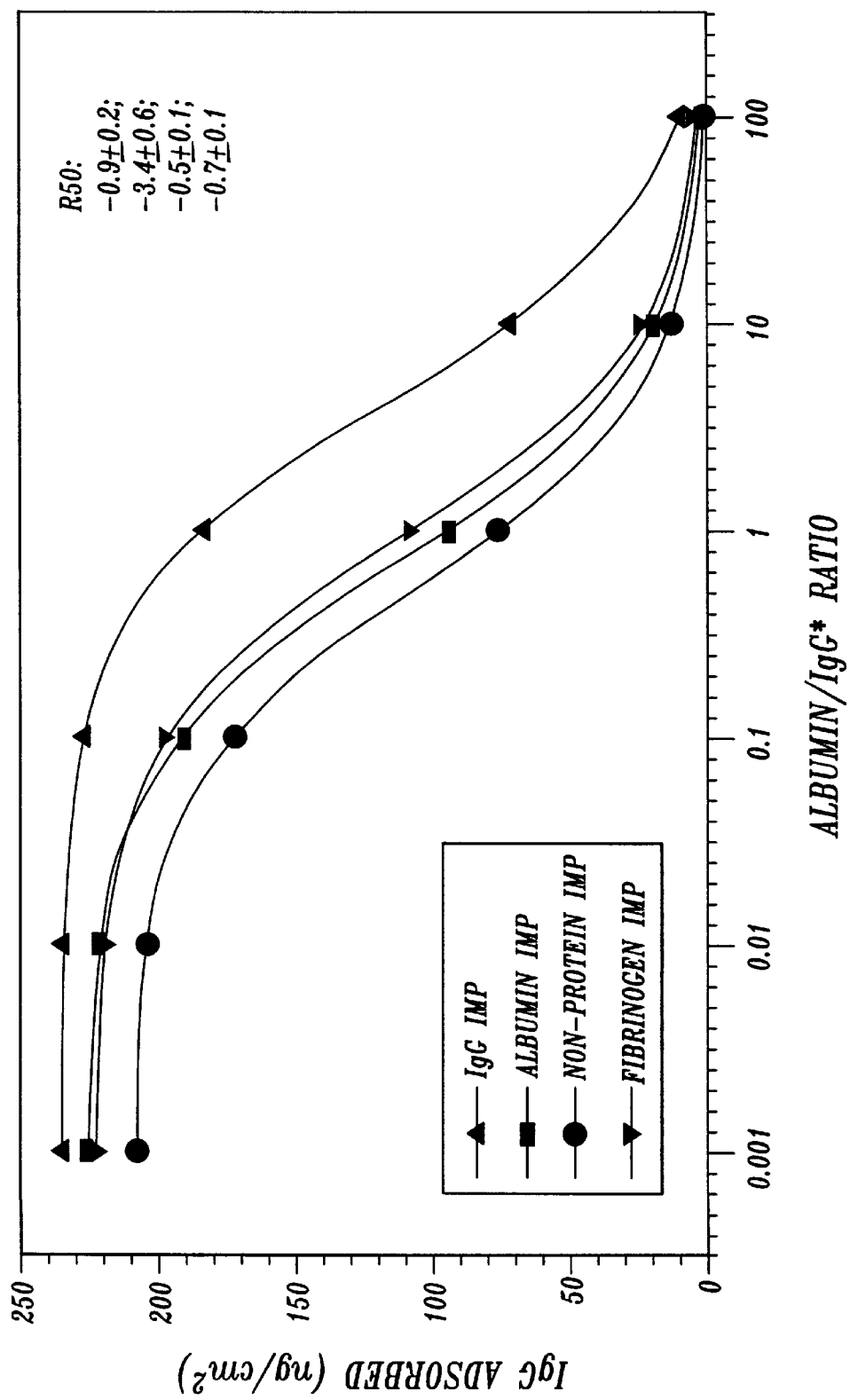
FIG. 29 shows competitive adsorption of $^{125}I$ labeled IgG (*) against unlabeled albumin on template-imprinted surfaces. Data are averages of triplicated samples. Error bars are omitted for clarity. Kaleidagraph™ was used to fit a curve to an equation. The ratio of unlabelled protein to labelled protein required to cause a 50% reduction in the maximum IgG adsorption (R50) was determined for each template-imprinted surface: albumin imprint (0.9±0.2); IgG imprint (3.4±0.6); fibrinogen imprint (0.7±0.1) and non-protein imprint (0.5±0.1). The R50 value is indicative of the binding affinity of the labelled protein to a template-imprinted surface.

Competitive adsorption of a binary protein mixture showed a highly preferential adsorption of template protein 24, albumin (BSA) (FIG. 28) or IgG (FIG. 29), onto its own imprint. The curve of BSA imprinted surface 12 adsorbing BSA and that of IgG imprinted surface 12 adsorbing IgG are always shifted towards the end of higher competing to labeled protein ratio, while the curves for protein imprinted surface 12 adsorbing non-template protein as well as control sugar imprint share another trend. These data indicate that more competing proteins are needed to compete with template proteins 24 to "crowd out" the latter's adsorption to their imprinted surface 12. The data is best evaluated by determining the ratio required to cause a 50% reduction in the maximum labeled protein adsorption ($R_{50}$). If the two proteins have equal affinity for surface 12 being tested, the $R_{50}$ value would occur at a concentration ratio of 1 (equal concentrations of proteins). If labeled protein has a greater affinity for surface 12 than does the competing protein, the $R_{50}$ would occur at a concentration greater than 1. Therefore, the high affinity of template proteins 24 (BSA or IgG) for their corresponding imprinted surfaces 12 (BSA imprinted surface or IgG imprinted surface, respectively) is demonstrated by significantly increased $R_{50}$ values.

Figure 30:
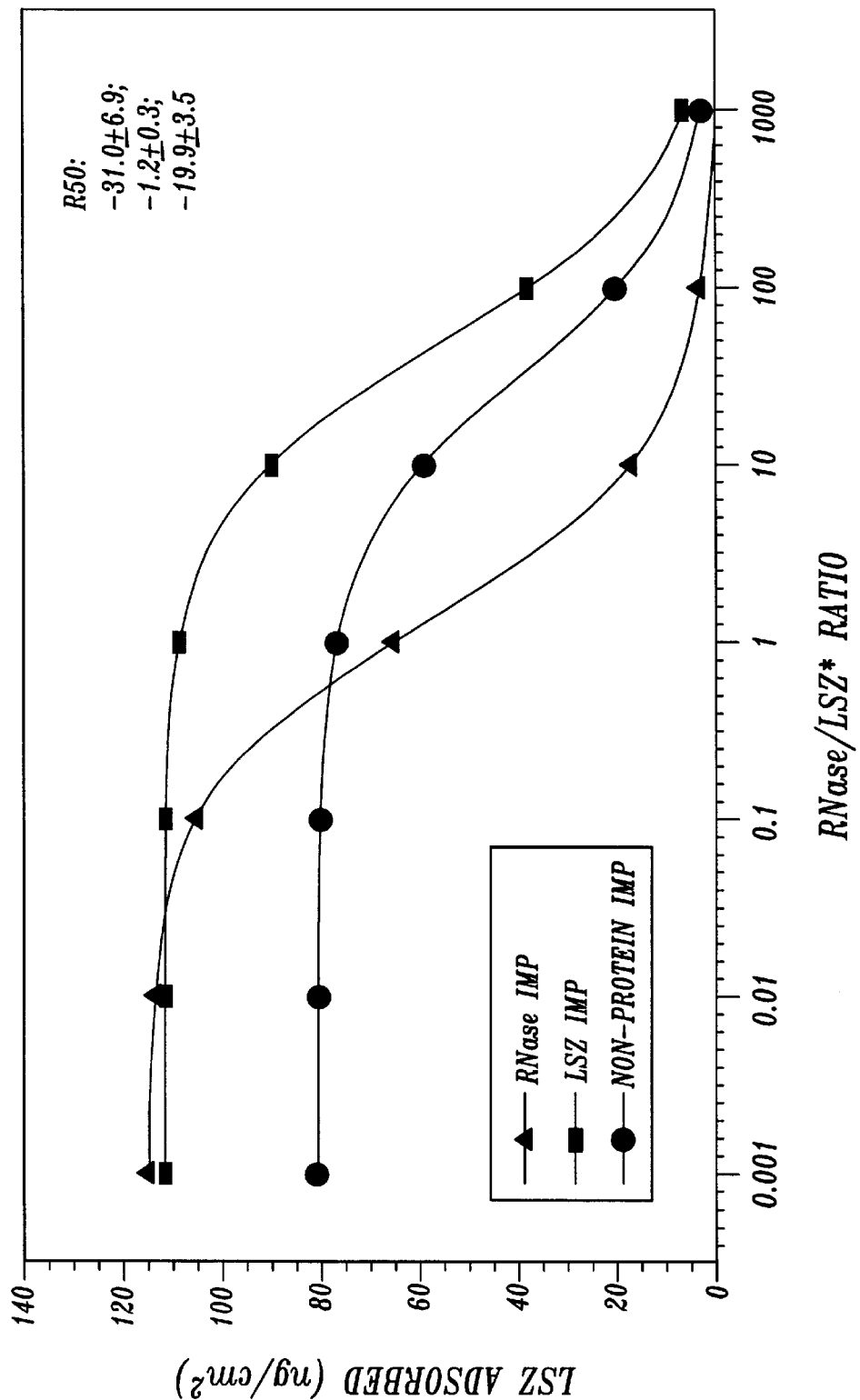
FIG. 30 shows competitive adsorption of $^{125}I$ labeled lysozyme (LSZ)(*) against ribonuclease A (RNase) on template-imprinted surfaces. Data are averages of triplicated samples. Error bars are omitted for clarity. Kaleidagraph™ was used to fit a curve to an equation. The ratio of unlabelled protein to labelled protein required to cause a 50% reduction in the maximum lysozyme adsorption (R50) was determined for each template-imprinted surface: lysozyme imprint (31.0±6.9); ribonuclease imprint (1.2±0.3) and non-protein imprint (19.9±3.5).
Figure 31:
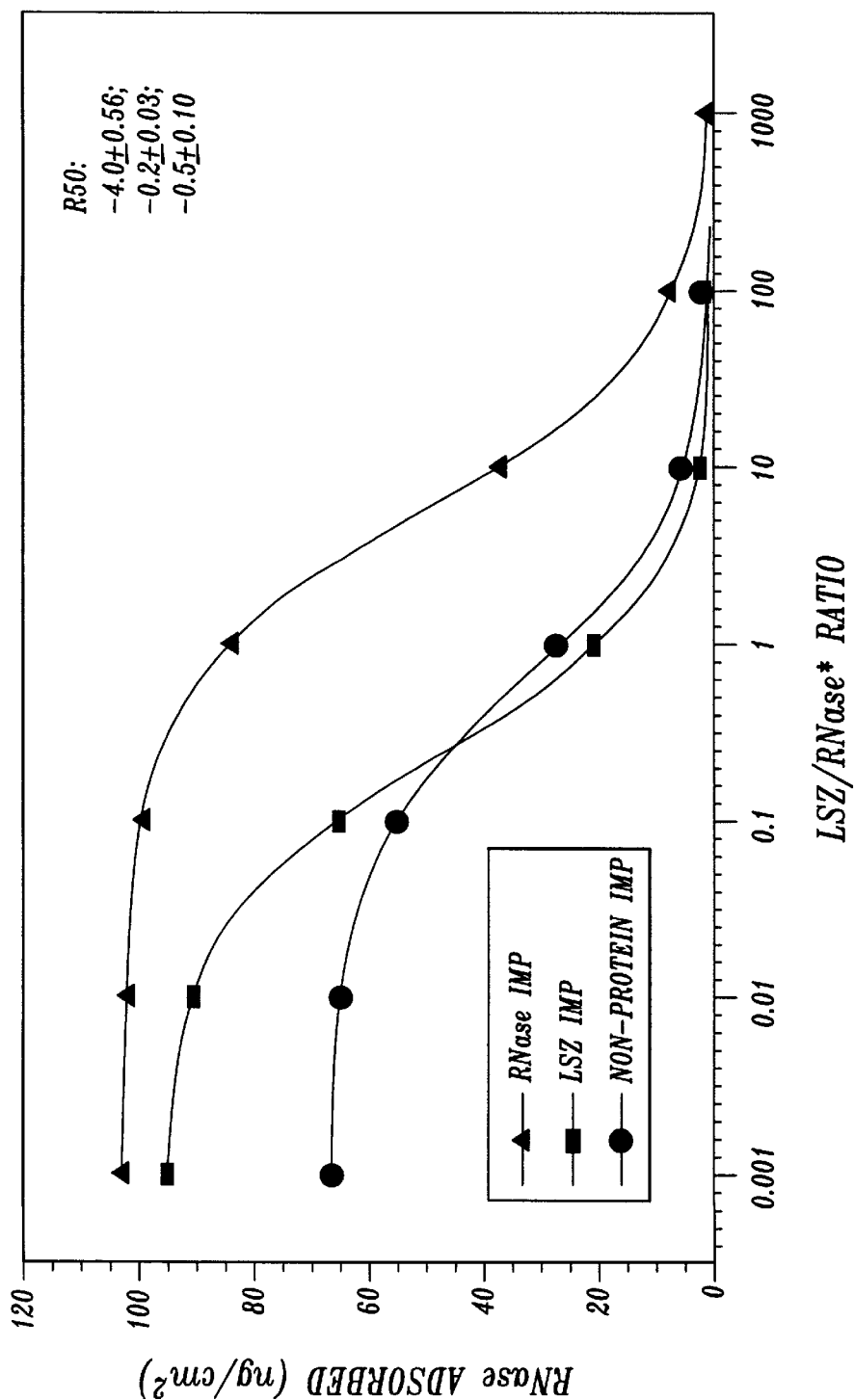
FIG. 31 shows competitive adsorption of $^{125}I$ labeled ribonuclease (Rnase) (*) against LSZ on template-imprinted surfaces. Data are averages of triplicated samples. Error bars are omitted for clarity. Kaleidagraph™ is used to fit a curve to an equation. The ratio of unlabelled protein to labelled protein required to cause a 50% reduction in the maximum ribonuclease adsorption (R50) was determined for each template-imprinted surface: ribonuclease imprint (4.0±0.6); lysozyme imprint (0.2±0.03); and non-protein imprint (0.5±0.10).

To further investigate the degrees of specificity in this protein recognition, lysozyme (LSZ) and ribonuclease A (Rnase) were template imprinted, both of which have a comparable molecular weight, dimension, structural rigidity and isoelectric point, and then performed competitive adsorption of LSZ and RNase on the imprinted surfaces 12. As shown in FIGS. 30 and 31, a pronounced selectivity is observed for an imprint surface 12 to recognize/adsorb its template protein 24 against a competing protein. A big shift occurs between the curve for LSZ imprinted surface 12 and that of RNase imprinted surface 12 in adsorbing either LSZ (~26-fold increase of $R_{50}$ for LSZ imprinted surface vs. RNase imprinted surface) or RNase (20-fold $R_{50}$ increase for RNase imprinted surface vs. LSZ imprinted surface). Similarly, the difference between RNase imprinted surface 12 and the sugar imprint control in adsorbing RNase against LSZ is significant ($R_{50}$ ratio: 4.0/0.5). However, LSZ imprinted surface 12 and the non-protein imprint has a relatively similar tendency in adsorbing LSZ against RNase, as shown by the close $R_{50}$ values (31.0/19.9). This phenomenon supports the hypothesis that differences between the dimensions of two proteins decides their surface reactivity with the template imprints. The smaller RNase molecule is probably able to slip into indentations 14 imprinted by LSZ and thus compete effectively with LSZ molecules for their binding sites, but it is harder for the bigger LSZ molecules to fill in the RNase-imprinted indentations 14, and consequently they act as poor competing proteins against RNase for RNase imprinted surface. Considering the Å order difference in size between RNase (38×28×22 Å) and LSZ (45×30×30 Å), this recognition of our protein imprints is of high specificity.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for forming a template-imprinted structure comprising:
    (a) depositing a layer of sugar onto a first supporting surface bearing a plurality of templates;
    (b) forming a plasma-deposited layer by depositing plasma onto said sugar layer;
    (c) affixing said plasma-deposited layer to a second supporting surface; and
    (d) removing said first supporting surface and said templates.

2. The method of claim 1 wherein said first supporting surface is selected from the group consisting of mica, glass and silicon wafer.

3. The method of claim 2 wherein said first supporting surface is mica.

4. The method of claim 1 wherein said templates are selected from the group consisting of cells, proteins, peptides and nucleic acids.

5. The method of claim 1 wherein said sugar is selected from the group consisting of trehalose, sucrose, lactose, mannose, maltose, fructose, glucose and galactose.

6. The method of claim 5 wherein the sugar is trehalose.

7. The method of claim 1 wherein said plasma-deposited layer is formed by a method selected from the group consisting of Radio Frequency Glow Discharge, direct current glow discharge plasma deposition, pulsed glow discharge plasma deposition and microwave glow discharge plasma deposition.

8. The method of claim 7 wherein said plasma-deposited layer is deposited by Radio Frequency Glow Discharge.

9. The method of claim 1 wherein said plasma-deposited layer is affixed to said second supporting surface by an adhesive.

10. The method of claim 9 wherein said adhesive is an epoxy resin.

11. The method of claim 1 wherein said second supporting surface is a surface of a medical prosthesis.

12. The method of claim 1 wherein said second supporting surface is a surface of a microchip.

* * * * *

UNITED STATES PATENT AND TRADEMARK OFFICE
CERTIFICATE OF CORRECTION

PATENT NO.   : 6,131,580
DATED        : October 17, 2000
INVENTOR(S)  : B.D. Ratner et al.

It is certified that error appears in the above-identified patent and that said Letters Patent is hereby corrected as shown below:

Column 1,
Line 6, after "Apr. 17, 1998." insert the following paragraph:
-- This invention was funded by the Natioanl Institutes of Health, grant number RR01296, and the National Science Foundation, grant number EEC-9529161. The United States government has certain rights in the invention. --

Signed and Sealed this

Nineteenth Day of March, 2002

Attest:

JAMES E. ROGAN
Attesting Officer
Director of the United States Patent and Trademark Office